United States Patent
Lipscomb et al.

(10) Patent No.: US 6,658,946 B2
(45) Date of Patent: Dec. 9, 2003

(54) METHOD OF DETECTING FLUID FLOW THROUGH A CONDUIT

(75) Inventors: James H. Lipscomb, Kennett Square, PA (US); Larry Jurik, deceased, late of Elmhurst, IL (US), by Anna Jurik, legal representative; Bernard Katz, Rockaway, NJ (US); Michael J. Keating, Blairstown, NJ (US); Stone Klengler, Escondido, CA (US); John J. Kotlarik, Lake Geneva, WI (US); Mieczyslaw Wroblewski, Lake Forest, IL (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 10/214,161

(22) Filed: Aug. 8, 2002

(65) Prior Publication Data

US 2002/0189324 A1 Dec. 19, 2002

Related U.S. Application Data

(62) Division of application No. 09/794,255, filed on Feb. 28, 2001.
(60) Provisional application No. 60/185,741, filed on Feb. 29, 2000.

(51) Int. Cl.$^7$ .................. G01F 22/02; G01F 15/075; G01F 1/34
(52) U.S. Cl. ................ 73/861.42; 73/861.44; 702/47
(58) Field of Search .............. 73/861.42, 861.44, 73/861.08, 168, 37; 702/47; 138/104; 417/63

(56) References Cited

U.S. PATENT DOCUMENTS

| 3,095,120 A | * | 6/1963 | Steiner et al. ............... 222/1 |
| 3,756,078 A | | 9/1973 | Yamasaki et al. |
| 3,818,757 A | | 6/1974 | Brown |
| 3,935,735 A | | 2/1976 | Lee |
| 4,003,243 A | * | 1/1977 | Blu et al. ................. 73/61.52 |
| 4,025,846 A | | 5/1977 | Franz et al. |

(List continued on next page.)

FOREIGN PATENT DOCUMENTS

| EP | 0981048 A2 | 2/2000 |
| GB | 2276240 A | 9/1994 |
| JP | 62-298768 | 12/1987 |
| JP | 10-019620 | 1/1998 |
| WO | WO 9222800 A1 | 12/1992 |
| WO | WO 9715809 A1 | 5/1997 |
| WO | WO 9930170 A1 | 6/1999 |
| WO | WO 9947906 A1 | 9/1999 |
| WO | WO 00/45161 A1 | 8/2000 |

*Primary Examiner*—Thomas P. Noland
(74) *Attorney, Agent, or Firm*—Rothwell, Figg, Ernst & Manbeck, P.C.; Charles B. Cappellari, Esq.

(57) ABSTRACT

A sensor for detecting contact of a fluid delivery probe with a fluid surface and for detecting fluid flow through the probe includes a first electrode disposed along a fluid flow path of the probe upstream from a distal tip of the probe and a second electrode longitudinally spaced and electrically isolated from the first electrode and disposed at the distal tip of the probe. An oscillating signal is transmitted through the first electrode, and at least a portion of the signal is received through the second electrode. Through changes in the received signal due to the distal tip of the probe coming into contact with a fluid surface or due to fluid flow through the conduit between the first and second electrodes, fluid surface contact and fluid flow can be detected. A pressure sensor can be employed to monitor internal fluid pressure within the fluid conduit of the fluid delivery probe as a secondary, redundant device for detecting fluid flow through the conduit.

8 Claims, 15 Drawing Sheets

U.S. PATENT DOCUMENTS

| | | | | |
|---|---|---|---|---|
| 4,166,388 A | | 9/1979 | Sun et al. | |
| 4,204,427 A | | 5/1980 | Gothe et al. | |
| 4,208,909 A | | 6/1980 | Maltby et al. | |
| 4,235,106 A | | 11/1980 | Maltby et al. | |
| 4,326,851 A | | 4/1982 | Bello et al. | |
| 4,347,740 A | | 9/1982 | Townsend | |
| 4,347,741 A | | 9/1982 | Geiger | |
| 4,442,719 A | | 4/1984 | Allen et al. | |
| 4,446,744 A | | 5/1984 | Bearcroft | |
| 4,459,857 A | | 7/1984 | Murray et al. | |
| 4,475,406 A | | 10/1984 | Ansaldi et al. | |
| 4,499,640 A | | 2/1985 | Brenton et al. | |
| 4,499,641 A | | 2/1985 | Fleckenstein | |
| 4,515,015 A | | 5/1985 | Kuhlman | |
| 4,536,711 A | | 8/1985 | King et al. | |
| 4,551,785 A | | 11/1985 | Kröner | |
| 4,589,077 A | | 5/1986 | Pope | |
| 4,676,100 A | | 6/1987 | Eichberger | |
| 4,739,492 A | * | 4/1988 | Cochran | 324/445 X |
| 4,778,451 A | | 10/1988 | Kamen | |
| 4,790,378 A | | 12/1988 | Montgomery et al. | |
| 4,850,805 A | * | 7/1989 | Madsen et al. | 417/63 X |
| 4,864,857 A | | 9/1989 | Koon | |
| 4,970,468 A | | 11/1990 | Ishizawa et al. | |
| 4,977,786 A | | 12/1990 | Davis | |
| 4,988,975 A | | 1/1991 | Nap | |
| 5,013,529 A | | 5/1991 | Itoh | |
| 5,045,286 A | | 9/1991 | Kitajima et al. | |
| 5,048,335 A | | 9/1991 | Marsh et al. | |
| 5,049,878 A | | 9/1991 | Stern | |
| 5,083,470 A | | 1/1992 | Davis et al. | |
| 5,121,632 A | | 6/1992 | Keeler et al. | |
| 5,212,992 A | | 5/1993 | Calhoun et al. | |
| 5,245,873 A | | 9/1993 | Fathauer et al. | |
| 5,304,347 A | | 4/1994 | Mann et al. | |
| 5,311,769 A | | 5/1994 | Hetzel | |
| 5,341,100 A | | 8/1994 | Taylor | |
| 5,365,783 A | | 11/1994 | Zweifel | |
| 5,443,791 A | | 8/1995 | Cathcart et al. | |
| 5,451,940 A | | 9/1995 | Schneider et al. | |
| 5,468,453 A | | 11/1995 | Holt et al. | |
| 5,493,922 A | | 2/1996 | Ramey et al. | |
| 5,495,130 A | | 2/1996 | Schneider | |
| 5,499,545 A | | 3/1996 | Kimura et al. | |
| 5,512,247 A | | 4/1996 | Bonacina et al. | |
| 5,529,754 A | | 6/1996 | Bonacina et al. | |
| 5,546,005 A | | 8/1996 | Rauchwerger | |
| 5,550,059 A | | 8/1996 | Boger et al. | |
| 5,554,937 A | | 9/1996 | Sanders et al. | |
| 5,559,339 A | | 9/1996 | Domanik et al. | |
| 5,582,798 A | | 12/1996 | Meltzer | |
| 5,600,997 A | | 2/1997 | Kemp et al. | |
| 5,610,527 A | | 3/1997 | Yamaguchi | |
| 5,611,240 A | | 3/1997 | Yamaguchi | |
| 5,612,227 A | | 3/1997 | Inoue et al. | |
| 5,639,426 A | | 6/1997 | Kerr et al. | |
| 5,648,727 A | | 7/1997 | Tyberg et al. | |
| 5,662,388 A | * | 9/1997 | Wuerth et al. | 303/3 |
| 5,665,601 A | | 9/1997 | Kilmer | |
| 5,672,050 A | | 9/1997 | Webber et al. | |
| 5,675,259 A | | 10/1997 | Arndt et al. | |
| 5,715,786 A | * | 2/1998 | Seiberth | 73/119 A |
| 5,739,598 A | | 4/1998 | Zatler et al. | |
| 5,750,881 A | | 5/1998 | Dorenkott et al. | |
| 5,814,275 A | | 9/1998 | Lewis et al. | |
| 5,843,378 A | | 12/1998 | El-Hage et al. | |
| 5,855,851 A | | 1/1999 | Matsubara et al. | |
| 5,919,706 A | | 7/1999 | Tajima | |
| 5,973,415 A | | 10/1999 | Brenner et al. | |
| 6,016,697 A | | 1/2000 | McCulloch et al. | |
| 6,060,320 A | | 5/2000 | Dorenkott et al. | |
| 6,062,091 A | | 5/2000 | Baumoel | |
| 6,073,488 A | | 6/2000 | Byatt et al. | |
| 6,100,094 A | | 8/2000 | Tajima | |
| 6,121,049 A | | 9/2000 | Dorenkott et al. | |
| 6,161,956 A | * | 12/2000 | Jerkel | 366/160.4 |
| 6,283,719 B1 | * | 9/2001 | Frantz et al. | 417/63 X |
| 6,478,547 B1 | * | 11/2002 | Savard et al. | 417/53 |
| 6,490,920 B1 | | 12/2002 | Netzer | 73/304 C |

* cited by examiner

METHOD OF DETECTING FLUID FLOW THROUGH A CONDUIT

This application is a divisional of U.S. patent application Ser. No. 09/794,255, filed Feb. 28, 2001, which claims the benefit of U.S. Provisional Application No. 60/185,741, filed Feb. 29, 2000, the entire disclosure of which is incorporated by reference.

BACKGROUND OF THE INVENTION

This invention relates to a system and method for verifying the movement of an amount of fluid through a fluid delivery probe and/or for detecting a fluid surface within a container that is entered by the fluid delivery probe.

Automated analyzers are commonly used by clinical laboratories and in health science research to assay and determine inter alia the presence or amount of a particular analyte or group of analytes in a biological sample. Typical biological samples for assaying include blood, urine, cerebrospinal fluid, pus, seminal fluid, sputum, stool, plants, water and soil. Analytes commonly targeted in biological samples include antibodies, antigens, nucleic acids, toxins and other chemicals. Clinicians especially prefer automated analyzers over manual procedures because of their high-throughput capabilities, reduced labor expenses, and the limits they place on human error that can lead to false or misleading results. To be most useful, an analyzer preferably automates both the sample preparation and sample processing steps of an assay.

Sample preparation may be initiated by an automated fluid transfer system which transfers a fluid sample from a sample container to a reaction vessel for analysis. The automated fluid transfer system may also be used to transfer one or more assay reagents from their respective containers or associated reservoirs into the sample-holding reaction vessel. After conducting the appropriate sample processing steps for a given assay, the contents of the reaction vessel may be examined by the automated analyzer to determine the presence or amount of at least one specifically targeted analyte. Detecting a targeted analyte in the sample might provide an indication that a particular pathogenic organism is present in the sample, or it might indicate a specific disease condition or state useful for determining or adapting a treatment regimen.

The fluid transfer system typically includes a fluid delivery probe operatively carried on a robotically controlled arm to perform aspiration and dispensing functions required for the transfer process and a pump coupled to the probe by a conduit system. During a fluid transfer operation, the robotic arm, under the command of a system controller, positions the fluid delivery probe above a sample or reagent container and moves the probe into the container until the tip of the probe reaches the fluid surface in the container. It is desirable that the distal tip of the probe be maintained right at the fluid surface to avoid ingesting air into the probe during aspiration and to avoid possible cross-contamination that can occur if the probe is unnecessarily submerged into the fluid and fluid residue is carried on the exterior of the probe from one sample to another. Accordingly, a desirable feature of an automated fluid delivery probe is a means by which contact of the probe tip with the fluid surface can be detected as the probe is being lowered into a fluid-containing vessel.

With the probe tip maintained at the fluid surface, a pump, such as a syringe type pump, is activated to draw an amount of sample or reagent fluid from the container into the probe. The amount of fluid aspirated will correspond to the volume and number of aliquots to be dispensed from the probe. The fluid delivery probe is thereafter moved into a position above a reaction vessel and a precise aliquot of fluid is dispensed. To ensure that accurate results are obtained in the tests, a predetermined volume of the sample must be accurately aspirated and dispensed into the reaction vessel. Accordingly, another desirable feature of an automated fluid delivery probe is automated verification of fluid dispensed from the probe.

Different devices and methods for automatically determining when a probe tip has contacted a fluid surface in a container have been proposed in the available literature. For example, some surface detection sensors operate on the basis of capacitance. The probe, if made from a conductive, e.g., metal, conduit, will exhibit a finite amount of electrical capacitance. When the probe tip contacts a fluid surface, the higher dielectric constant and greater surface area of the fluid results in a small, but measurable, increase in the capacitance of the probe.

Other surface detection mechanisms for incorporation onto a fluid delivery probe include two or more electrodes which may comprise tubular elements arranged coaxially with each other (see, e.g., U.S. Pat. Nos. 5,304,347 and 5,550,059) or elongated conductors extending along the length of the probe and arranged in a spaced, parallel relationship (see, e., U.S. Pat. Nos. 5,045,286 and 5,843,378). When the probe contacts a fluid surface, the fluid, which contacts both electrodes simultaneously, electrically couples the electrodes to each other. If a voltage is applied across the electrodes the electrical coupling caused by the electrodes contacting the fluid surface results in a measurable change in the voltage drop across the electrodes.

U.S. Pat. Nos. 5,013,529 and 5,665,601 describe surface detection devices which incorporate a pressure sensor connected to a fluid line through which constant pressure gas is expelled through the tip of the probe. When the tip contacts the fluid surface, thereby blocking the gas emitting orifice (i.e., the end opening of the probe), a measurable change in the pressure is exhibited. U.S. Pat. No. 6,100,094 describes a surface detection device which includes an optic emitter which emits light axially through, or alongside, a tip. The light is reflected from the fluid surface back into the tip to a light sensor disposed within the tip. The amount of light reflected back to the light sensor detectably changes when the tip contacts the fluid surface.

The prior art surface detection sensors described above each suffer from certain shortcomings. For example, achieving adequate accuracy and repeatability with capacitive surface sensors can be difficult because the change in capacitance exhibited when a probe contacts a fluid surface can be very small and thus difficult to detect. This is especially true where the fluid is a conductive fluid with a low dielectric value. Furthermore, because of the small capacitance changes exhibited, capacitive surface detection sensors can be susceptible to inaccuracies due to fluctuating stray capacitances caused by adjacent moving structures or changes in the amount of fluid contained in the probe and/or container.

Dual electrode surface detection devices constructed to date, with side-by-side or coaxial arrangement of the electrodes, are complex and cumbersome. Surface detection devices that emit constant pressure gas can cause disturbances and even bubbling and/or atomization of the fluid. The effectiveness of optic sensors can be diminished due to residue or other buildup on the optic emitter and/or receiver.

Other devices and methods are described in the available literature for verifying aspiration and/or delivery of a fluid from the probe. For example, U.S. Pat. No. 6,121,049 describes a system wherein the pressure needed to hold up a column of aspirated fluid in the probe can be measured and compared to a predetermined standard to determine if a proper amount of fluid has been aspirated. By verifying a proper aspiration, a proper subsequent fluid delivery can, theoretically, be inferred. U.S. Pat. No. 5,559,339 describes a system which includes optical sensors, each with an emitter-receiver pair, disposed adjacent the pipette tip. Fluid flowing from the tip breaks the electromagnetic beam between the emitter and receiver, thereby indicating the flow of fluid. The duration of fluid flow can be monitored to determine if a proper amount of fluid has been dispensed.

Such fluid flow verification devices suffer from shortcomings which can limit their effectiveness. Pressure sensors that measure the amount of pressure required to hold up a column of aspirated fluid may be effective for confirming a proper aspiration of fluid, but, because fluid delivery can be interrupted by system leaks or occlusions blocking the probe, such sensors do not necessarily provide confirmation of proper fluid delivery. Furthermore, such devices are useful only for fluid delivery procedures that involve aspiration of fluid into the probe prior to delivery of the fluid from the probe into a reaction vessel. Such devices will not provide confirming information for fluid transfer systems in which fluid is pumped directly from a reservoir through the fluid delivery probe and into a reaction vessel without first being aspirated from another container.

As with surface detection devices that employ optic emitters and receivers, the effectiveness of the optic sensors employed to verify fluid flow can be diminished by residual build-up or other debris interfering with the emission or reception of the electromagnetic beam.

Accordingly the devices and methods described heretofore in the prior art are susceptible to further improvement. Moreover, although surface detection and fluid delivery verification are important features of a consistently accurate automated fluid delivery probe, the prior art does not describe a simple, effective, and accurate method and device for providing the combined capabilities of surface detection and fluid delivery verification in a single fluid delivery probe. Finally, the prior art does not describe a fluid delivery verification method or device in which secondary, redundant means are employed for verifying fluid delivery to guard against erroneous indications of proper fluid delivery.

SUMMARY OF THE INVENTION

The present invention overcomes the shortcomings of and is an improvement over surface detection and fluid delivery verification apparatuses described above.

In particular, the present invention comprises a sensor mechanism that includes a pair of longitudinally spaced, electrically isolated electrodes forming portions of a fluid flow conduit of a fluid delivery probe. The first electrode is disposed along a portion of the fluid delivery probe upstream from the tip, and the second electrode is disposed at the tip of the probe. An oscillating signal is transmitted by the first electrode, which functions as a transmitting antenna, and some portion of the transmitted signal is received by the second electrode, which functions as a receiving antenna. The characteristics of the signal received by the second electrode, i.e., the amplitude and/or the phase difference of the signal, will change when the tip of the fluid delivery probe contacts a fluid surface and/or if there is fluid flow through the conduit between the first and second electrodes. By monitoring the received signal, the sensor, along with its associated interface circuitry, can provide both surface detection and fluid delivery verification. Depending on the characteristics of the fluid, i.e., whether the fluid is an ionic or non-ionic fluid, the amplitude or the phase of the received signal may exhibit a more pronounced change. In any event, the sensor is effective for surface detection and fluid delivery verification for any type of fluid.

The sensor can be enhanced by incorporating a pressure sensor for monitoring internal system pressure during fluid delivery. By determining whether a pressure signal profile obtained during an intended fluid delivery compares favorably with the profile that would be expected for proper delivery of a particular fluid, the fluid delivery can be verified. Thus, the pressure sensor provides a secondary, redundant verification to compliment the fluid delivery verification provided by monitoring the signal received by the second electrode.

In a preferred manner of verifying a proper fluid delivery, the amplitude of the signal received by the second electrode is monitored or the phase difference between the transmitted and received signals is monitored (the amplitude and phase difference signals will be generically referred to as the "tip signal") during an intended fluid delivery. In particular, the tip signal is integrated from a time approximating the intended initiation of fluid delivery to a time approximating the intended termination of fluid delivery. In addition the tip signal variability is analyzed from the initiation time to the termination time. The tip integral and the tip signal variability are compared to accepted values experimentally determined for proper delivery of the particular fluid being delivered, and, if they are not within acceptable limits, an error signal is generated.

The tip signal is indicative of the continuity of fluid flow between the first and second electrodes. An irregularity in the tip signal, which is indicative of a discontinuity in fluid flow between the electrodes (due to, e.g., pump malfunction, probe blockage, air bubbles in the dispensed or aspirated fluid, insufficient fluid available for dispensing), will result in a tip signal integral and/or tip signal variability that is not within accepted limits. On the other hand, a tip signal integral and tip signal variability that are within accepted limits are indicative of a regular tip signal over the duration of the intended fluid delivery and thus are indicative of a proper fluid delivery.

Similarly, a pressure signal is also obtained and analyzed to verify a proper fluid delivery. In particular, the initiation of a fluid delivery will result in a detectable jump in the pressure signal from a steady state, quiescent value, and termination of fluid delivery will result in a detectable drop in pressure toward the steady state value. The jump and drop in the fluid pressure signal are located and the elapsed time between the jump and drop, termed the pulse width, is determined. In addition, the pressure signal is integrated over the pulse width. The pressure integral and the pulse width are compared to accepted values experimentally determined for proper delivery of the particular fluid being delivered, and, if they are not within acceptable limits, an error signal is generated.

The pressure signal reflects the continuity of the pressure level during an intended fluid delivery. An irregularity in the pressure signal (due to, e.g., pump malfunction, probe blockage, air bubbles in the dispensed or aspirated fluid, insufficient fluid available for dispensing), will result in a pressure signal integral and/or pulse width that is not within accepted limits. On the other hand, a pressure signal integral and pulse width that are within accepted limits are indicative of a regular pressure signal of proper duration during the intended fluid delivery and thus are indicative of a proper fluid delivery. Accordingly, the pressure sensor provides a secondary fluid delivery verification to compliment the fluid delivery verification provided by the first and second electrodes.

Having two electrodes, longitudinally spaced from each other and forming portions of the fluid delivery probe conduit, the sensor of the present invention is simple in construction and unobtrusive and adds little to the overall size of the fluid delivery probe. Moreover, the sensor does not suffer from the deficiencies encountered with prior art sensors described above. In particular, the sensor of the present invention is not sensitive to stray system capacitance, is effective regardless of the ionic properties of the fluid, does not rely upon potentially unreliable optic sensors, and does not emit a gas pressure stream that can disturb the fluid to be aspirated.

Other objects, features, and characteristics of the present invention, including the methods of operation and the function and interrelation of the elements of structure, will become more apparent upon consideration of the following description and the appended claims, with reference to the accompanying drawings, all of which form a part of this disclosure, wherein like reference numerals designate corresponding parts in the various figures.

DETAILED DESCRIPTION OF THE PREFERRED EMBODIMENT

Figure 1:
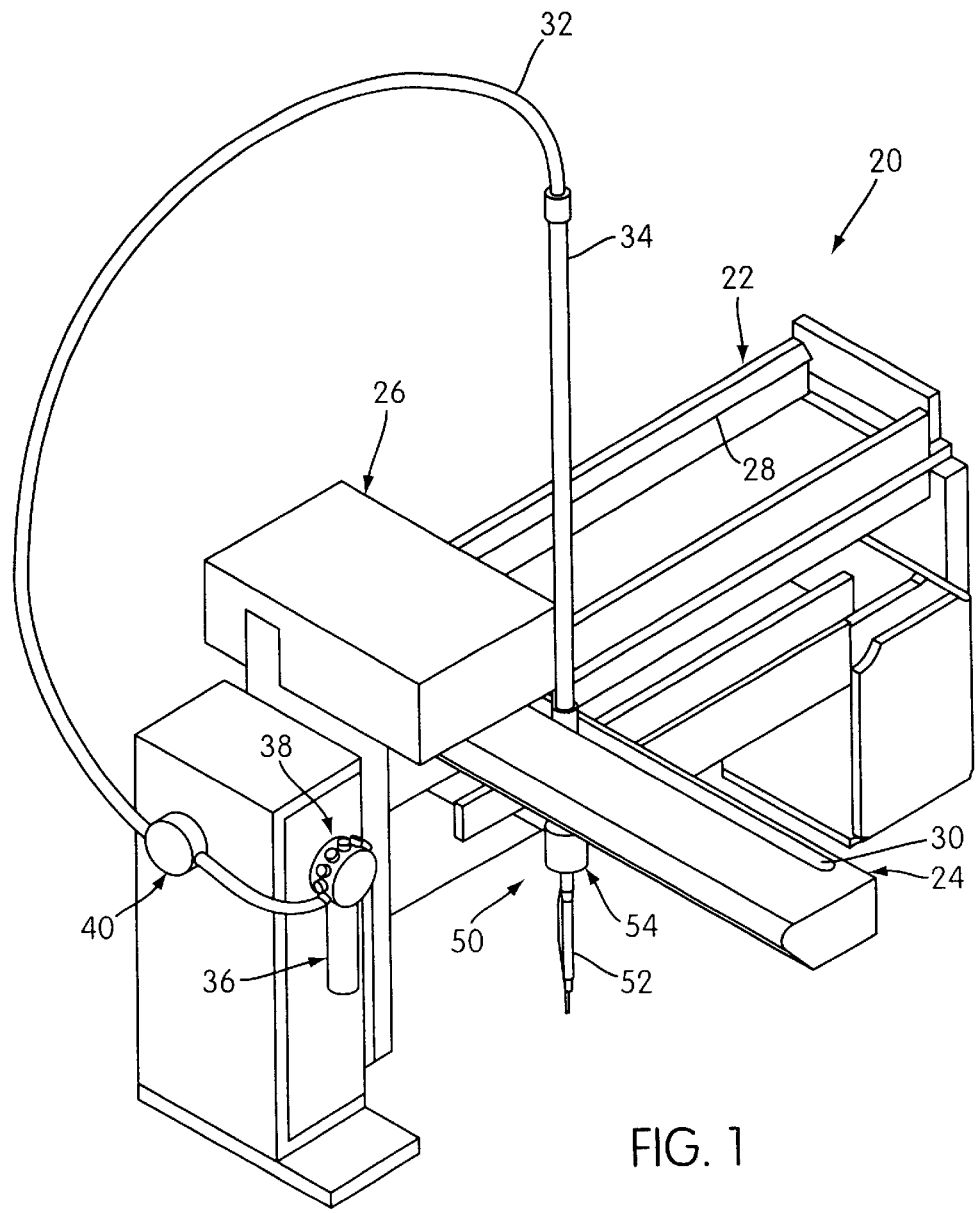
FIG. 1 is a perspective view of a robotic substance transfer mechanism.

A robotic substance transfer mechanism with which a fluid dispense and fluid surface verification system according to the present invention can be operationally combined is generally designated by reference number 20 in FIG. 1. The robotic substance transfer mechanism 20 into which the dispense and surface verification system of the present invention can be incorporated may be an off-the-shelf device, such as a Model No. RSP 9000 Robotic Sample Processor available from Cavro Inc. of Sunnyvale, Calif. On the other hand, while the dispense and surface verification system of the present invention is described herein primarily in the context of its incorporation into a robotic substance transfer mechanism, such as that shown in FIG. 1, the system can as well be incorporated into any mechanism which performs an automated fluid delivery function and in which fluid dispense verification and/or fluid surface detection is required or advantageous.

The robotic substance transfer mechanism 20 includes a fluid delivery probe 50 having a fluid delivery conduit assembly 52 and mounted on a gantry assembly to provide X, Y, and Z motion. In particular, the fluid delivery probe 50 is mounted on a longitudinal translation boom 24, and the longitudinal translation boom 24 is mounted on and supported by a lateral translation boom 22. X-Y motion in a horizontal plane can be effected by motors disposed within a housing 26 for moving the fluid delivery probe 50 along the longitudinal translation boom 24 and the lateral translation boom 22. In the illustrated embodiment, a translation motor (not shown) within the housing 26 powers a driving device that cooperates with a track 28 formed along the lateral translation boom 22 to move the housing 26 and the longitudinal translation boom 24 reciprocally along the lateral translation boom 22. Movement of the fluid delivery probe 50 along the longitudinal translation boom 24 may be effected by means of a motor (not shown) housed in the housing 26 and coupled to, for example, an endless belt disposed within the longitudinal translation boom 24 and attached to the fluid delivery probe 50 or a lead screw threadedly coupled to the fluid delivery probe 50 for moving the probe axially along the screw as the screw rotates about its own axis. Another motor (not shown) is carried on the substance transfer mechanism 20 along the longitudinal translation boom 24 and is coupled to the fluid delivery probe 50, for example, by a lead screw or a rack and pinion arrangement, for effecting Z-axis, vertical movement of the fluid delivery probe 50.

The fluid delivery conduit assembly 52 extends into a tube protector block 54 disposed below the longitudinal translation boom 24. A rigid tube extension 34, preferably made from stainless steel tubing, extends upwardly through a pipette slot 30 formed in the longitudinal translation boom 24, terminating at a position above the longitudinal translation boom 24.

Figure 2:
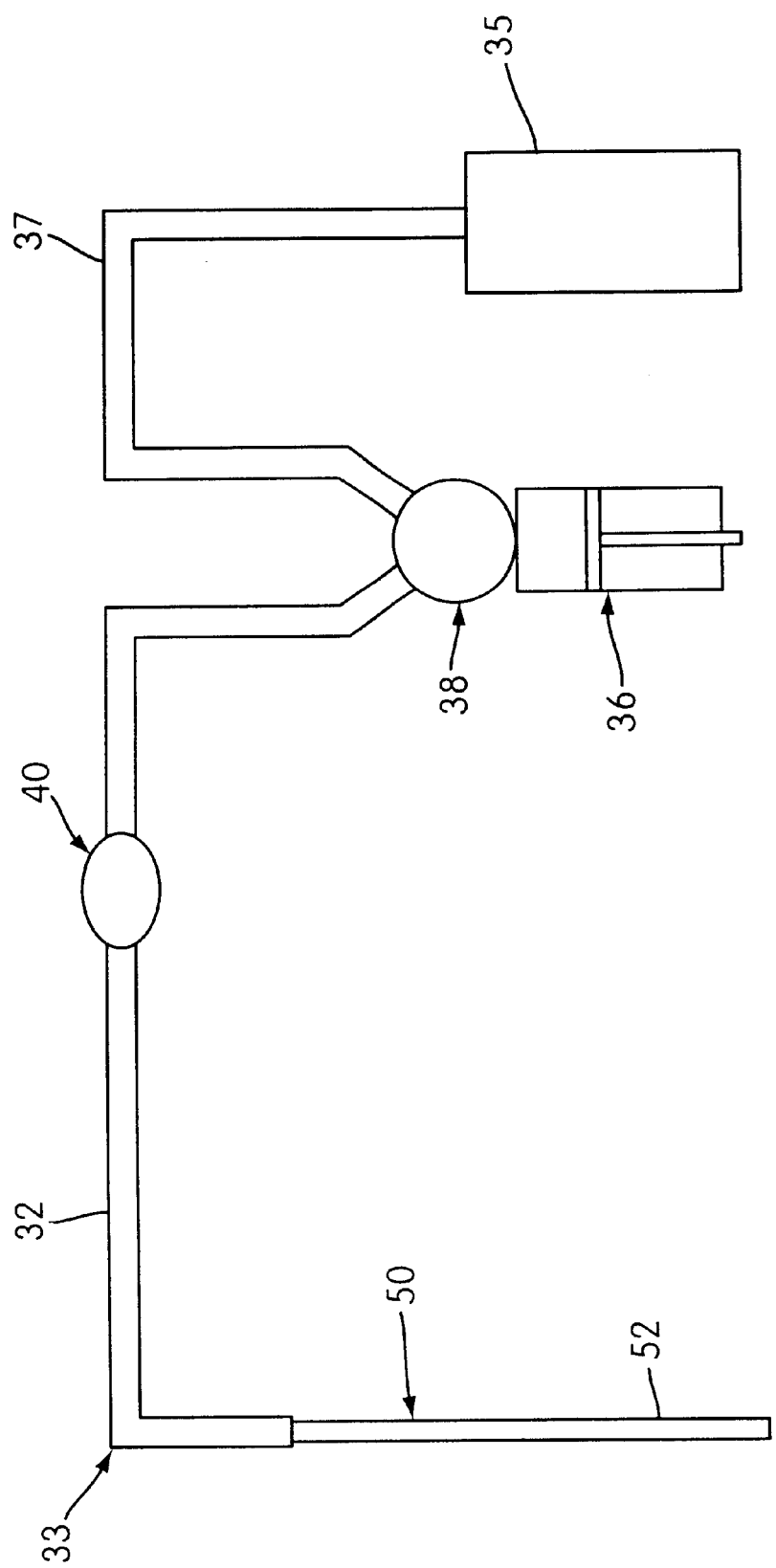
FIG. 2 is a schematic view of a fluid delivery system embodied within a substance transfer mechanism.

Fluid delivery is performed by a pump 36, which forces fluid flow through a flexible tube 32, preferably made from polytetrafluoroethylene (PTFE), and into the rigid tube extension 34 and the fluid delivery conduit assembly 52. The flexible tube 32, rigid extension 34 and the fluid delivery conduit assembly 52 together form at least a portion of a fluid conduit system 33 through which the pump 36 moves fluid dispensed by the fluid delivery probe 50. In particular, pump 36 is preferably a syringe pump, such as a Cavro Model Number XL 3000 Modular Digital Pump. Other types of pumps may be used as well. Pump 36 may be coupled to an optional, multi-port (preferably three-port) rotary valve 38. The flexible tube 32 is connected to an output port of the valve 38 (or directly to the pump 36 if no valve is employed) and extends to and is connected at the proximal end of the rigid tube extension 34 (see FIGS. 1 and 2). In the exemplary embodiment shown in the figures, fluid delivery line 37 carries fluid from a fluid reservoir or container, generally represented at 35, to the valve 38. A multi-port rotary valve allows the pump to be switched from the reservoir 35, from which fluid may be drawn into the fluid delivery system by pump 36, to the fluid delivery probe 50, thereby allowing fluid in the fluid delivery system to be delivered (i.e., dispensed) by the pump 36 through the fluid delivery probe 50. A multi-port rotary valve allows multiple fluid reservoirs and/or multiple fluid delivery probes to be alternately coupled to one another via a pump.

Fluid may also be drawn into the fluid conduit system 33 by the pump 36 directly through the fluid delivery conduit assembly 52 operatively positioned in a container of fluid. Proper positioning of the fluid delivery conduit assembly 52 is facilitated by the surface detection capability of the dispense and surface verification system, as will be described hereinbelow.

The dispense and surface verification system of the present invention includes an in-line pressure sensor 40 located along the flexible tube 32 between the pump 36 and the fluid delivery probe 50. Pressure sensor 40 detects when a fluid (including a pure liquid or a solution, mixture, slurry, suspension, etc.) is moved by the pump 36 along the portion of the fluid conduit system 33 defined by the fluid delivery conduit assembly 52, the rigid tube extension 34, and the flexible tube 32. In particular, sensor 40 is able to differentiate resistance to fluid flow based on fluid composition. Thus, the pressure indicated by sensor 40 would be detectably different for a liquid moved through the conduit than for air moved through the conduit. A preferred sensor is a Honeywell model 26PCBFG5G flow-through pressure sensor because it is a self-calibrating sensor that compensates for changes in ambient temperature and because it is a robust device with silicone sealing which protects electronic strain gauges attached to a pressure-sensitive diaphragm located inside the sensor. The function and operation of the pressure sensor 40 will be described in further detail below.

Figure 3:
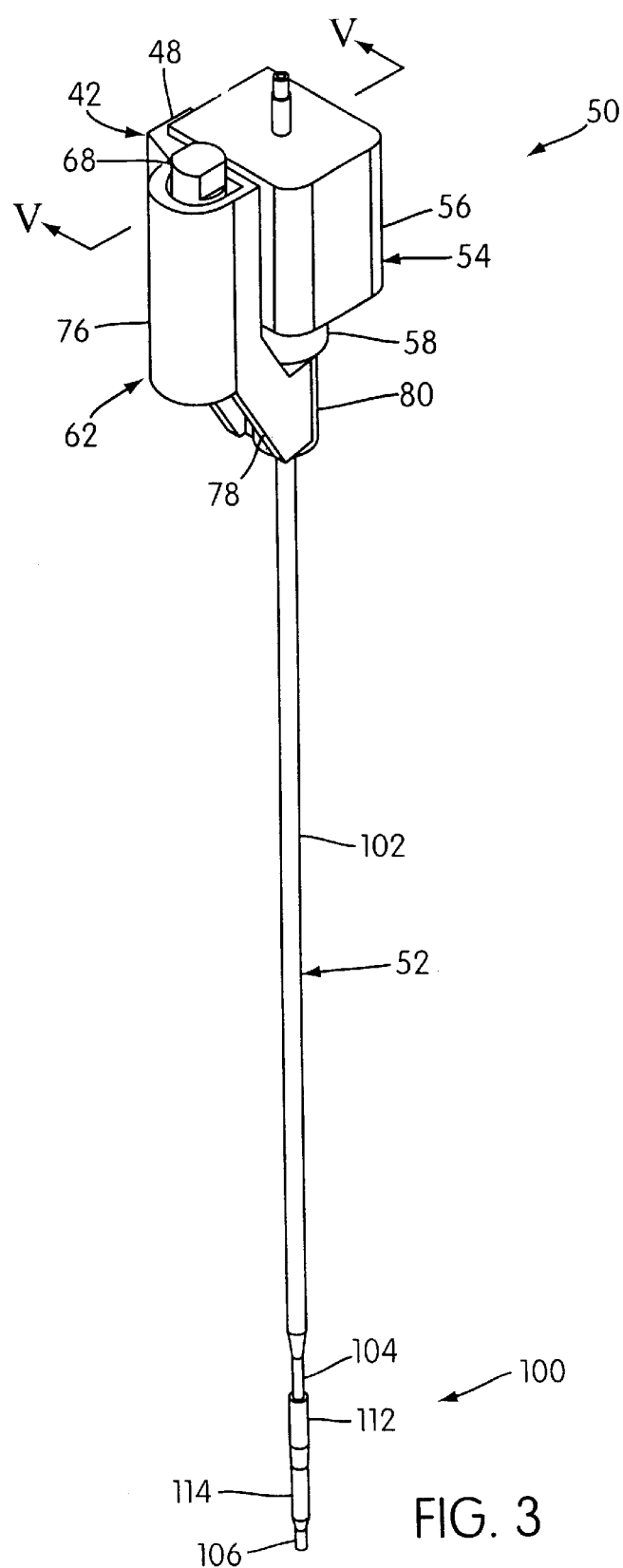
FIG. 3 is a perspective view of a fluid delivery probe incorporating a fluid dispense and fluid surface verification device according to the present invention.
Figure 4:
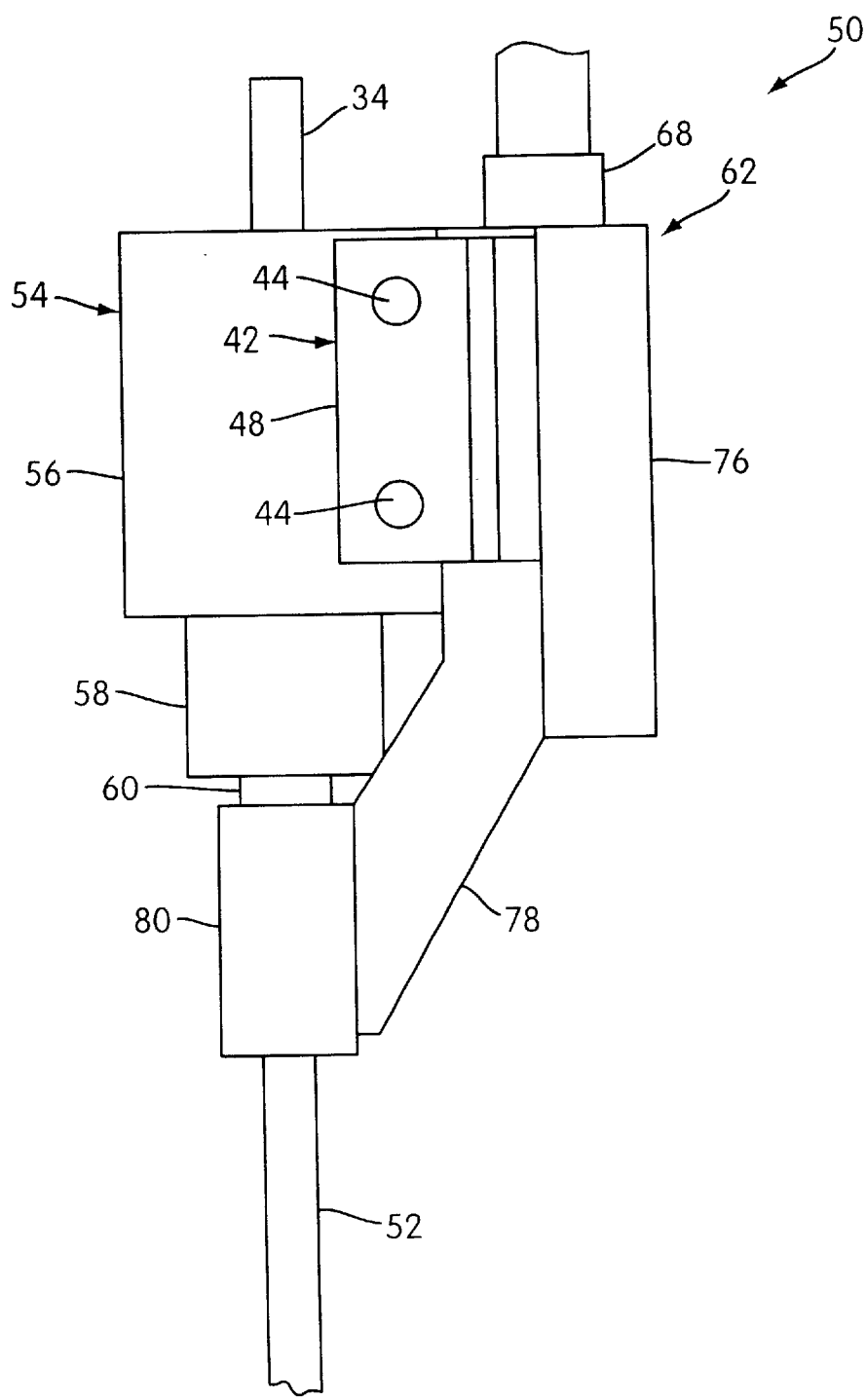
FIG. 4 is a partial side elevation of an upper portion of the fluid delivery probe.
Figure 5:
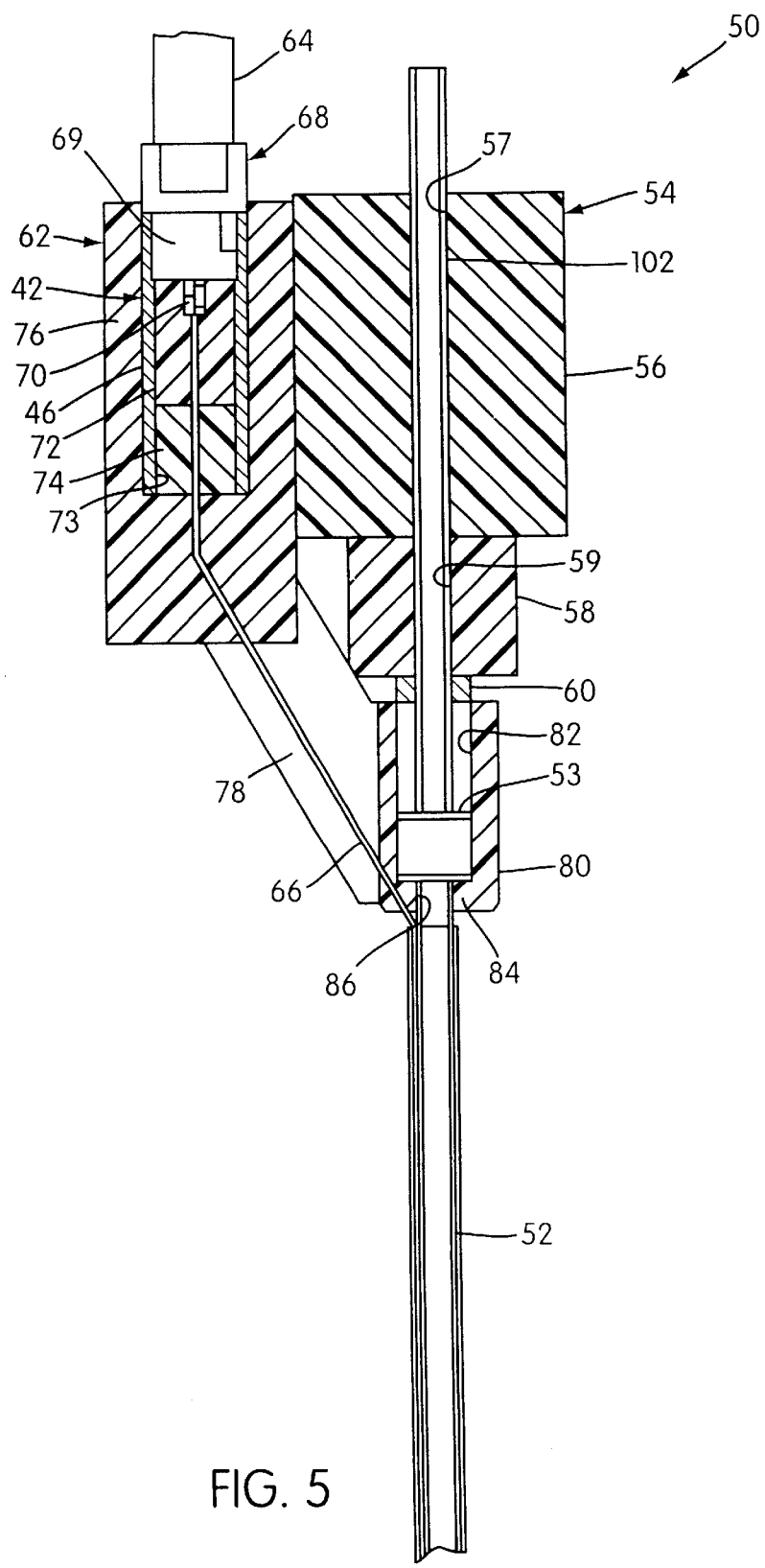
FIG. 5 is a partial transverse cross-section of the fluid delivery probe along the line V—V in FIG. 3.

The fluid delivery probe 50 will now be described with reference to FIGS. 3–5. The tube protector 54 is comprised of an upper portion 56, shown in the drawings as having the general shape of a rectangular solid, and a lower portion 58, having a generally cylindrical shape as shown in the drawings. A through-hole 57 is formed through the upper portion 56, and a through-hole 59 is formed through the lower portion 58. The aligned through-holes 57 and 59 receive a transfer tube 102 of the fluid delivery assembly 52 with a sliding fit between the tube 102 and the through-holes 57 and 59. The upper portion 56 and the lower portion 58 of the tube protector 54 are preferably formed from a polymeric material and most preferably from an injection molded thermoplastic, such as Lexan®.

A cable connector housing 62 is attached at one portion thereof to the tube protector 54 and at another portion thereof to the transfer tube 102. The cable connector housing 62 includes an upper portion 76, an angled portion 78, and a tube connecting portion 80. The cable connector housing 62 is also preferably formed from an injection molded thermoplastic, such as Lexan®. An extruded aluminum bracket 42 forms a part of the cable connector housing 62 by an insert molding process. A flange 48 of the bracket 42 projects from the cable connector housing 62 and is attached to the tube protector 54 by means of one or more fasteners 44 extending through openings formed in the flange 48 and into the tube protector 54.

A cylindrical opening 82 is formed in the tube connecting portion 80. A bottom end 84 of the tube connecting portion 80 has a through-hole 86 formed therein and thereby provides a partial closure of the cylindrical opening 82. A stop element 53 is secured to the transfer tube 102 at an intermediate position along its length. In the preferred embodiment, both the stop element 53 and the transfer tube 102 are made from stainless steel, and the stop element 53 is secured to the transfer tube 102 by brazing. The dimensions of the transfer tube 102 (i.e., length, inside diameter, and outside diameter) will depend on the application. The cable connector housing 62 is attached to the transfer tube 102 by inserting the transfer tube 102 through the through-hole 86 until the stop element 53 is received within the opening 82, which is sized and shaped so as to conform to the stop element 53. The diameter of the through-hole 86 is smaller than the inside diameter of the cylindrical opening 82 and the outside diameter of the stop element 53. Therefore the stop element 53 bottoms out at the bottom end 84 of the tube connecting portion 80. The tube connecting portion 80 is secured to the stop element 53 and the transfer tube 102 by means of epoxy which fills the opening 82. A preferred epoxy is available from Master Bond, Inc. of Hackensack, N.J., product number EP 42HT.

In the illustrated embodiment, a plastic spacer element 60 is disposed between the lower portion 58 of the tube protector 54 and the tube connecting portion 80 of the cable connector housing 62. The lower portion 58 rests against the spacer element 60, and the spacer element 60 fills a gap created between the top of the tube connecting portion 80 and the bottom end of the lower portion 58 when the bottom end of the lower portion 58 contacts a top part of the angled portion 78, thereby blocking the lower portion 58 from contacting the top end of the tube connecting portion 80. Of course, if the geometries of the lower portion 58 and the tube connecting portion 80 are such that the lower portion 58 can rest directly on the tube connecting portion 80, without being blocked by the angled portion 78, the spacer element 60 may be omitted.

A blind opening 73 is formed in an upper portion 76 of the cable connector housing 62. In the preferred embodiment shown in the figures, a cylindrical section 46 of the bracket 42 forms the sides of the opening 73. A coaxial cable connector 68 is attached to an upper end of the upper portion 76 at the mouth of the opening 73, preferably by inserting a lower end 69 of the connector 68 into an upper end of the cylindrical section 46. A suitable cable connector is available from Lemo, Inc. of Santa Rosa, Calif., model number ERA0125DLL. An external coaxial cable 64 can be attached to the connector 68 for transmitting signals to the interface circuitry described below.

Figure 6:
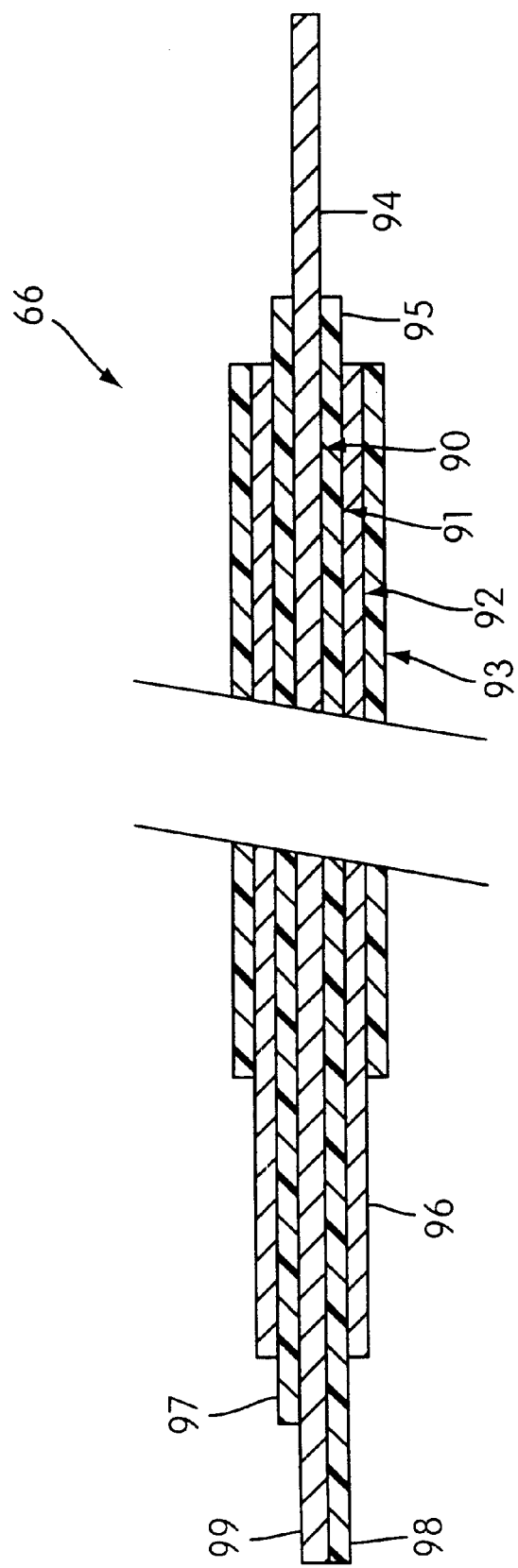
FIG. 6 is a longitudinal cross-section of a ribbon cable assembly used in conjunction with FIG. 7 is a transverse cross-section of the sensor assembly of the fluid delivery probe.

A coaxial ribbon cable 66 is electrically connected to the cable connector 68 by means of a ribbon connector interface 70 which is crimped onto an exposed end of the ribbon cable 66. FIG. 6 shows a longitudinal cross section of the ribbon cable 66. As shown in FIG. 6, the ribbon cable 66 comprises a multi-layer structure having at its center an electrically conductive core 90 running the entire length of the cable 66. Core 90 is preferably a copper strip having a preferred thickness of 0.003 inches and a preferred width of 0.03 inches. An inner insulation layer 91, preferably polyester, surrounds the core 90. A silver shielding layer 92 is sprayed onto the inner insulation layer 91 so as to completely surround the core 90 and the inner insulation layer 91. An outer insulation layer 93 of a Teflon®-type material is sprayed onto the silver layer 92 so as to completely surround the core 90, the inner insulation layer 91, and the silver shielding layer 92.

At one end of the cable 66 (the right end as shown in the figure), the inner and outer insulation layer 91, 93 and the silver shielding layer 92 are removed from the core 90 so as to present an exposed section 94 of the core 90. Exposed section 94 is attached to the connector 68 via the ribbon connector interface 70.

At the opposite end of the cable 66 (the left side as shown in the figure), the outer insulation layer 93, the silver shielding layer 92, and one half of the inner insulation layer 91 are removed from the cable 66 so as to present an exposed section 99 of the core 90 with a portion 98 of the inner insulation layer 91 bonded to one side thereof. To the immediate right of the exposed sections 98 and 99, portions of the silver shielding layer 92 and the outer insulation layer 93 are removed from the cable to form exposed section 97 of the inner insulation layer 91. To the immediate right of the exposed section 97, an exposed section 96 of the silver shielding layer 92 has the outer insulation layer 93 removed therefrom.

As can be appreciated, the layers at the opposite ends of the cable 66 are made into a tiered formation. The purpose of this tiered formation will be explained below.

The ribbon cable 66 is preferably insert molded into a lower end of the upper portion 76 of the cable connector housing 62 and thereafter extends into the opening 73. The cable connector 68 and the portion of the ribbon cable 66 extending into the opening 73 are secured to the cable connector housing 62 by means of epoxy filling the opening 73. In particular, the opening 73 is filled with a lower epoxy layer 74, preferably comprising Master Bond EP-21TDC/S silver epoxy, and an upper epoxy layer 72, preferably comprising Master Bond EP-30 epoxy. Two different types of epoxy are used to secure the ribbon cable 66, because the different epoxies react differently with the exposed and non-exposed sections of the cable 66. Master Bond EP-21TDC/S silver epoxy is used in the lower epoxy layer 74 because this type of epoxy is caustic and would damage the exposed portion 94 of the core 90 near the connector interface 70. On the other hand, the EP-30 epoxy used in the upper epoxy layer 72 is not caustic to the exposed portion 94, but will not adhere to exposed section 95 of the insulating protective layer 91. The EP-21TDC/S epoxy will adhere to the insulating protective layer 91 and thereby secure the covered portion of the ribbon cable 66 within the opening 73. The layer 91 on the ribbon cable 66 protects the core 90 of the cable 66 from the caustic effects of the EP-21TDC/S epoxy.

Alternatively, the cable 66 can be insert molded within the upper portion 76 of the cable connector housing 62 so that substantially only the exposed end 94 thereof extends into an opening in the upper portion 76 that is shorter in length than opening 73. Thus, the lower epoxy layer 74 can be eliminated and the cable can be set within the housing 62 by a single layer of non-caustic epoxy, such as Master Bond EP-30 epoxy.

Figure 7:
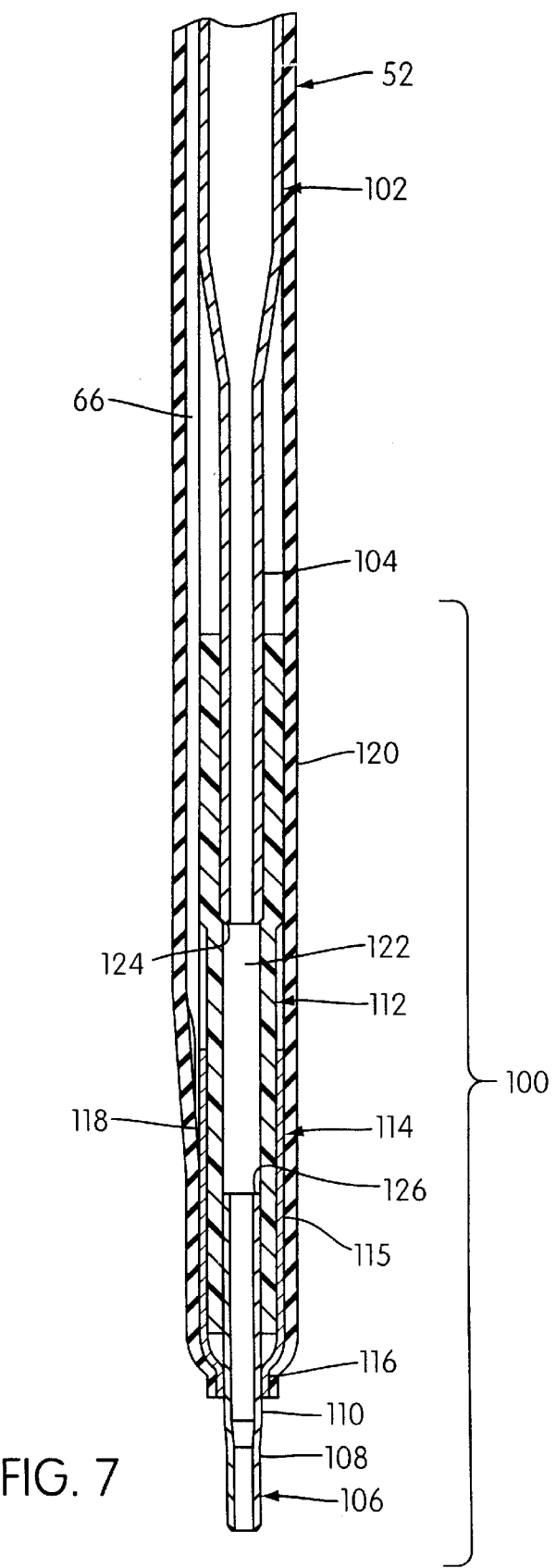

The details of the fluid delivery conduit assembly 52 will be described with reference to FIG. 7. The assembly 52 includes the transfer tube 102 extending down from the rigid tube extension 34 and through the tube protector 54 and the tube connecting portion 80 of the cable connector housing 62. As indicated above, the transfer tube 102 is preferably formed of stainless steel and includes a tapered tip 104 at a distal end thereof.

A sensor assembly 100 is arranged at the distal end of the transfer tube 102. The sensor assembly 100 includes an isolating sleeve 112 having one end thereof inserted over the tapered tip 104 of the transfer tube 102. The isolating sleeve 112 preferably comprises a tube constructed of polyethylene terephthalate (PET). Another suitable material for the isolating sleeve 112 is polytetrafluoroethylene (PTFE), although PTFE is less desirable than PET because it has been determined that protein deposits can form on PTFE, and these deposits are slightly conductive. A tip element 106 is inserted into an opposite end of the isolating sleeve 112 so that it is axially spaced from the distal end of the transfer tube 102. Tip element 106 is preferably a stainless steel tube having a variable outside diameter defining an upper section 110 and a lower section 108, whereby the upper section 110 has a greater outside diameter than the lower section 108. The size of the upper section 110 conforms to the size of commercially available material employed for the construction of the isolating sleeve 112. The lower section 108 was made to have a smaller inner and outer diameter in accordance with the size of the opening of a vessel into which the fluid delivery conduit assembly 52 is to deliver fluid. It is not necessary to the operation of the sensor assembly 100, however, that the tip 106 have two sections of different inner and/or outer diameters.

The isolating sleeve 112 is secured to the transfer tube 102 and the tip element 106 by means of epoxy, preferably Master Bond EP-42HT epoxy.

A tip interface element 114 is secured to a lower end of the isolating sleeve 112. The tip interface element 114, preferably formed of stainless steel, includes an upper, generally cylindrical section 115 having an inside diameter sized so as to snugly fit over the outer surface of the lower portion of the isolating sleeve 112, and a narrow neck section 116 at a lower end thereof having an inside diameter sized so as to snugly fit over the upper section 110 of the tip element 106. The inner surface of the cylindrical section 115 of the tip interface element 114 is secured to the outside of the isolating sleeve 112 by means of epoxy, preferably Master Bond EP-42HT epoxy. The neck section 116 is secured to the tip element 106 by means of a laser micro-weld. The coaxial ribbon cable 66 extends downwardly from the cable connector housing 62 along the outside of the transfer tube 102 and the isolating sleeve 112 and an exposed section 118 of the cable 66 is attached to the tip interface element 114. A cover sleeve 120 covers the sensor assembly 102, as will be described below.

Figure 8:
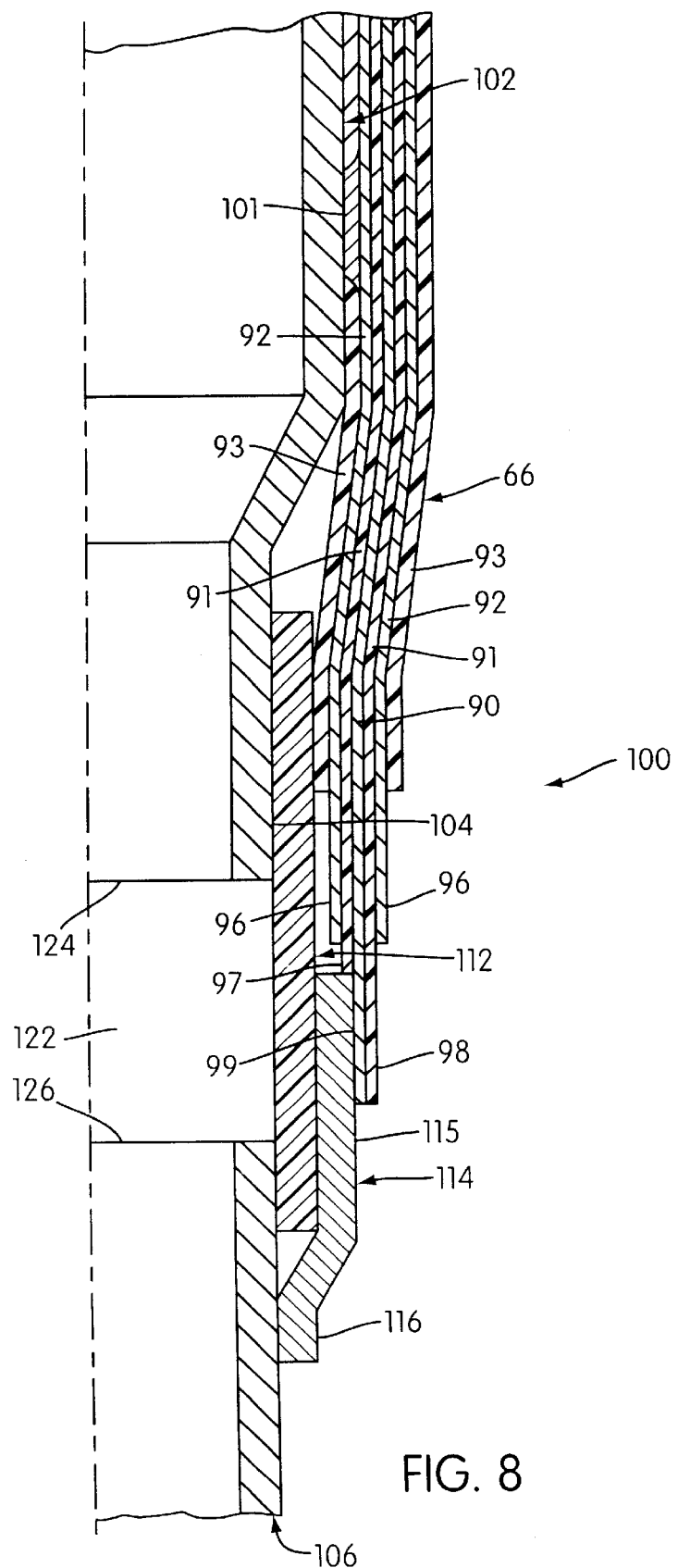
FIG. 8 is a partial transverse cross-section of the sensor assembly showing the ribbon cable assembly connected to the sensor assembly.

FIG. 8 shows an enlarged view of a longitudinal cross-section of the lower end of the sensor assembly 100 illustrating the preferred manner in which the coaxial ribbon cable 66 is attached to the assembly 100. For clarity, the cover sleeve 120 is not shown in FIG. 8.

As shown in FIG. 8, the exposed section 99 of the cable 66 is soldered to the upper section 115 of the tip interface element 114. The exposed section 98 of the insulation layer 91 on one side of the exposed section 99 opposite the side soldered to the tip interface element 114 minimizes noise (i.e., stray, unwanted electrical emissions, emi, emf) picked up by the core 90 and also provides a protective layer between the cover sleeve 120 (not shown in FIG. 8) and the exposed section 99. The short section 97 of the layer 91 provides a separation between the tip interface element 114 and section 96 of the silver shielding layer 92 to further limit noise within the cable 66 by preventing contact between tip interface element 114 and the silver shielding layer 92. The tiered configuration of the cable 66 formed by the exposed section 96 of the silver shielding layer 92 provides a less drastic transition between the thin end of the cable at exposed sections 98 and 99 and the full thickness of the cable 66 attached to the side of the transfer tube 102, thereby providing a relatively gradual transition to be covered by the sleeve 120. This makes it easier to fit the sleeve 120 over the assembly 100 and also eliminates drastic discontinuities in the thickness of the assembly 100 which can cause tears in the sleeve 120. The silver shielding layer 92 is grounded to the transfer tube 102 by exposing a portion of the silver shielding layer 92 and connecting the exposed portion to the transfer tube by silver solder or conductive silver epoxy, generally indicated at 101 in FIG. 8.

The tip element 106 is preferably coated, inside and out, with a non-stick material, such as Teflon®, available from E. I. du Pont de Nemours and Company. The purpose of the non-stick coating is to minimize hanging fluid drops clinging to the end of the tip element 106 and also to facilitate tip cleaning between fluid transfers.

The cover sleeve 120 covers and protects the sensor assembly 100 and the upper portions of the transfer tube 102 between the sensor assembly 100 and the tube protector 54 and further covers and protects the coaxial ribbon cable 66. The cover sleeve is preferably a resilient tube formed from PTFE that is fitted over the transfer tube 102 and the sensor assembly 100 by expanding it on a mandrel (not shown) or some similar expanding device and inserting the tube 102 and sensor assembly 100 into the expanded cover sleeve 120. Thereafter, the cover sleeve 120 is released from the expanding device, so that it snugly surrounds the tube 102 and sensor assembly 100. The inner surface of the cover sleeve 120 is preferably chemically etched to enhance the bond between the sleeve 120 and the transfer tube 102, and the cover sleeve 120 is preferably secured to the transfer tube 102 and the sensor assembly 100 by means of an epoxy, preferably Master Bond EP-42HT epoxy. Alternatively, the cover sleeve 120 may be formed from a heat shrinkable material and may be installed by any known method for installed such material.

Figure 9:
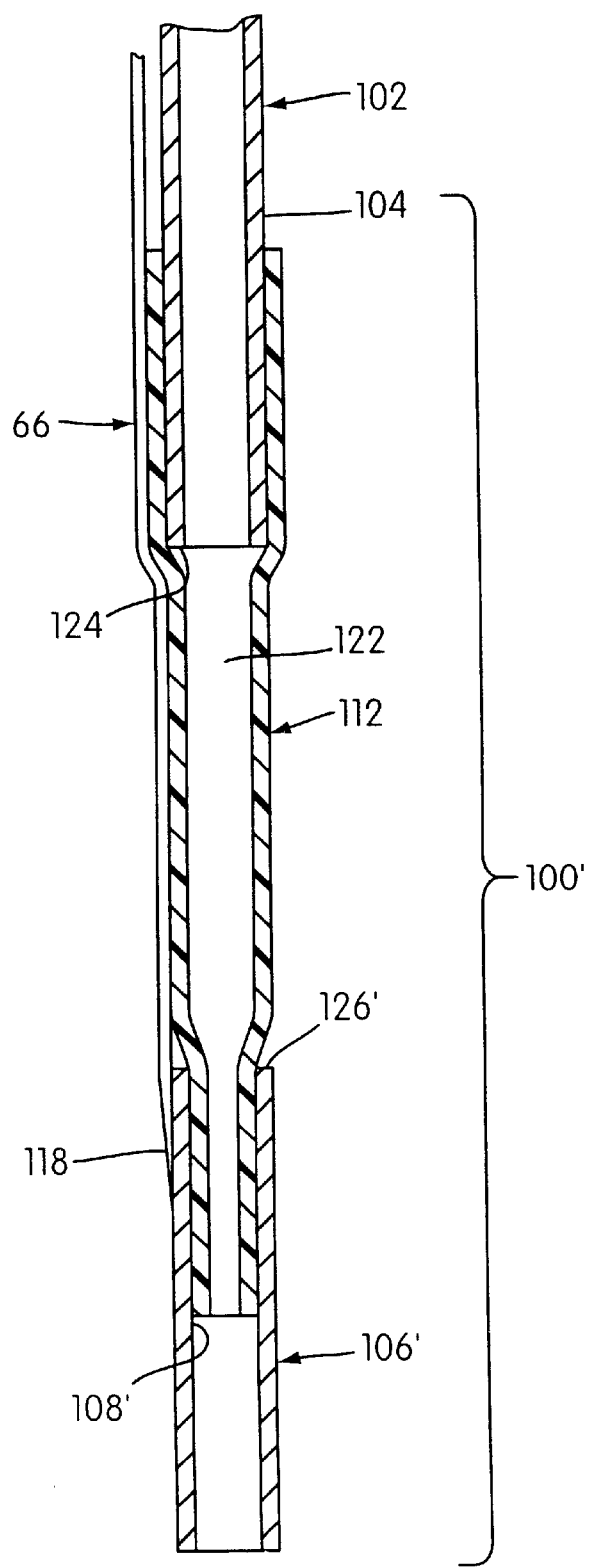
FIG. 9 is a transverse cross-section of an alternate embodiment of the sensor assembly of the fluid delivery probe.

An alternate, and presently preferred, arrangement of a sensor assembly is designated generally by reference number 100' in FIG. 9. The sensor assembly 100' of FIG. 9 (the cover sleeve 120 (see FIG. 7) is omitted from the FIG. 9 for simplicity in the illustration) is similar to the sensor assembly 100 shown in FIG. 7 and previously described, except that the tip element 106 and the tip interface element 114 are replaced by a single tip element 106' into which the isolating sleeve 112 is inserted as shown. The isolating sleeve 112 is secured to the tip element 106' by a suitable epoxy. The exposed section 118 of the ribbon cable 66 is attached, preferably by a micro spot weld, directly to the tip element 106'.

In general, the dispense and surface verification system functions as follows. The transfer tube 102 (FIG. 3) constitutes a first, or transmitting, electrode for transmitting an oscillating radio frequency (RF) signal that is generated by interface circuitry, as will be described below. The tip element 106 constitutes a second, or receiving, electrode that is electrically isolated from the transfer tube 102 (i.e., the first electrode) by means of the isolating sleeve 112. The tip element 106 functions as a receiver for receiving the signals transmitted by the transfer tube 102, and the received signals are transmitted to interface circuitry, as will be described in more detail below, by means of the coaxial ribbon cable 66 and the external cable 64 (FIG. 5).

When the fluid delivery conduit assembly 52 is neither dispensing a fluid nor in contact with a fluid surface, a certain steady state signal will be received by the tip element 106 and transmitted via the coaxial ribbon cable 66 to the interface circuitry 203. When the fluid delivery probe 50 is lowered by the robotic substance transfer mechanism 20 into a container of fluid so that the tip element 106 of the fluid delivery conduit assembly 52 contacts the surface of the fluid within the container, the receiving characteristics of the tip element 106 will change, and thus the nature of the received signal (i.e., the amplitude and/or the phase of the received signal) will also measurably change. By monitoring and detecting this change within the interface circuitry, contact with the fluid surface can be detected. When fluid surface contact is detected, an appropriate command signal is generated and transmitted to the motor(s) effecting vertical movement of the fluid delivery probe 50 to thereby stop further lowering of the probe 50.

The precise detection of the fluid surface and arresting of the vertical movement of the fluid delivery probe 50 is important for a number of reasons. One rather obvious reason is that it is desirable to arrest downward movement of the probe 50 prior to its contact with the bottom of the container, which could cause damage to the probe 50. Another reason is that if a significant portion of the end of the fluid delivery conduit assembly 52 is submerged in a reagent, the outer surface of the conduit assembly 52 will become coated with that reagent. Because the same robotic substance transfer device 20, and therefore the same conduit assembly 52, may be used to transfer different reagents from various reagent containers, it is necessary to clean the conduit assembly 52 between reagent transfers, typically by passing de-ionized water through the conduit assembly 52. If a significant portion of the outside of the conduit assembly 52 is coated with reagent, simply passing water through the conduit assembly 52 will not adequately clean the assembly if it is to be submerged into another reagent. Therefore, it is desirable to keep the tip of the conduit assembly 52 at the surface of the reagent fluid while the fluid is being drawn into the conduit assembly 52. Appropriate movement controls that are well known in the art may be employed to slightly lower the fluid delivery probe 50 while fluid is being drawn, thereby adjusting for the falling fluid surface within the container and maintaining the tip of the conduit assembly 52 at the fluid surface.

Delivery of fluid by the fluid delivery conduit assembly 52 can be monitored and verified, in part, by sensing fluid flow through the sensor assembly 100. More particularly, a section 122 of the isolating sleeve 112 between the distal end 124 of the transfer tube 102 and the proximal end 126 of the tip element 106 defines a measurement section 122. When fluid flows through the sensor assembly 100, that is from the transfer tube 102, through the measurement section 122, and ultimately through the tip element 106, the presence of fluid in the measurement section 122 between the transfer tube 102 and the tip element 106 detectably alters the nature of the signal transmission between the transfer tube 102 and the tip element 106. Thus, the signal received by the tip element 106 will be different from the steady state signal received by the tip element 106 before or after fluid passes through the sensor assembly 100, as will be described in further detail below.

If the fluid passing through the measurement section 122 is a conductive fluid, i.e., an ionic fluid, primarily the amplitude of the signal received by the tip element 106 will change from that of the steady state signal. On the other hand, if the fluid passing through the measurement section 122 is non-conductive, i.e., non-ionic, primarily the phase of the signal received by the tip element 106 will change from that of the steady state signal due to a change in the capacitance of the sensor assembly 100. In either case, by monitoring and assessing the nature and magnitude of the change in the received signal with the interface circuitry, as described in more detail below, the flow of fluid through the measurement section 122 can be verified, thereby verifying fluid delivery by the fluid delivery probe 52.

Those skilled in the art will appreciate that many fluids will exhibit characteristics that are neither completely ionic or non-ionic. That is, fluids may generate both conductive and capacitive reactive effects.

Confirmation of fluid delivery is facilitated by the in-line pressure sensor 40. That is, when both the sensor assembly 100 and the in-line pressure sensor 40 indicate that fluid is passing through the fluid delivery conduit assembly 52, fluid delivery is confirmed. On the other hand, if the in-line pressure sensor and the sensor assembly give inconsistent fluid delivery indications, an error, or fault detection, signal is generated. The specifics of the fault detection algorithm of the preferred embodiment will be described in detail below.

Moreover, the specific characteristics of the received tip signal and/or the pressure signal (i.e., the shapes of the signal profiles) may be fluid dependent and can be experimentally determined for each specific fluid. Thus, the signal profiles can be monitored during fluid delivery or during a tip wash procedure to verify that the proper fluid was delivered through the tip.

An alternative configuration for a fluid delivery probe including a fluid dispense and fluid surface verification sensor not shown in the drawing includes a fluid delivery tube with an elongated sensor rod having an outside diameter smaller than the inside diameter of the tube extending through the tube. The sensor rod has two conductive portions longitudinally spaced from one another and separated from each other by a substantially non-conductive portion. One conductive portion is preferably located at the distal end of the sensor rod if the sensor is to be used for fluid surface detection, and the other conductive portion is located above the distal conductive portion. The sensor rod may be coterminous with the tube, or the position of its distal end may vary with respect to the distal end of the tube, depending on the desired position of the tube with respect to the fluid surface when the fluid surface is detected. A signal-transmitting circuit, as described below, is electrically coupled to the upstream conductive portion of the sensor rod, and a signal-receiving circuit, as also described below, is electrically coupled to the distal conductive portion of the sensor rod. A signal, preferably RF, is transmitted from the upstream conductive portion of the sensor rod, and at least a portion of the transmitted signal is received by the signal-receiving circuit through the distal conductive portion of the sensor rod. In a like manner as generally described above, and to be described in further detail below, fluid dispense verification and fluid surface detection can be accomplished by monitoring one or more characteristics of the received signal. That is, the received signal will detectably change when either the distal conductive portion of the sensor rod contacts a fluid surface or when fluid flows through the tube around the sensor rod between the transmitting and receiving conductive portions of the sensor rod.

Interface Circuitry

The interface circuitry, discussed in more detail below, provides the "intelligence" for performing the fluid dispense verification and surface sensing functions described above and discussed in more detail below.

Figure 10:
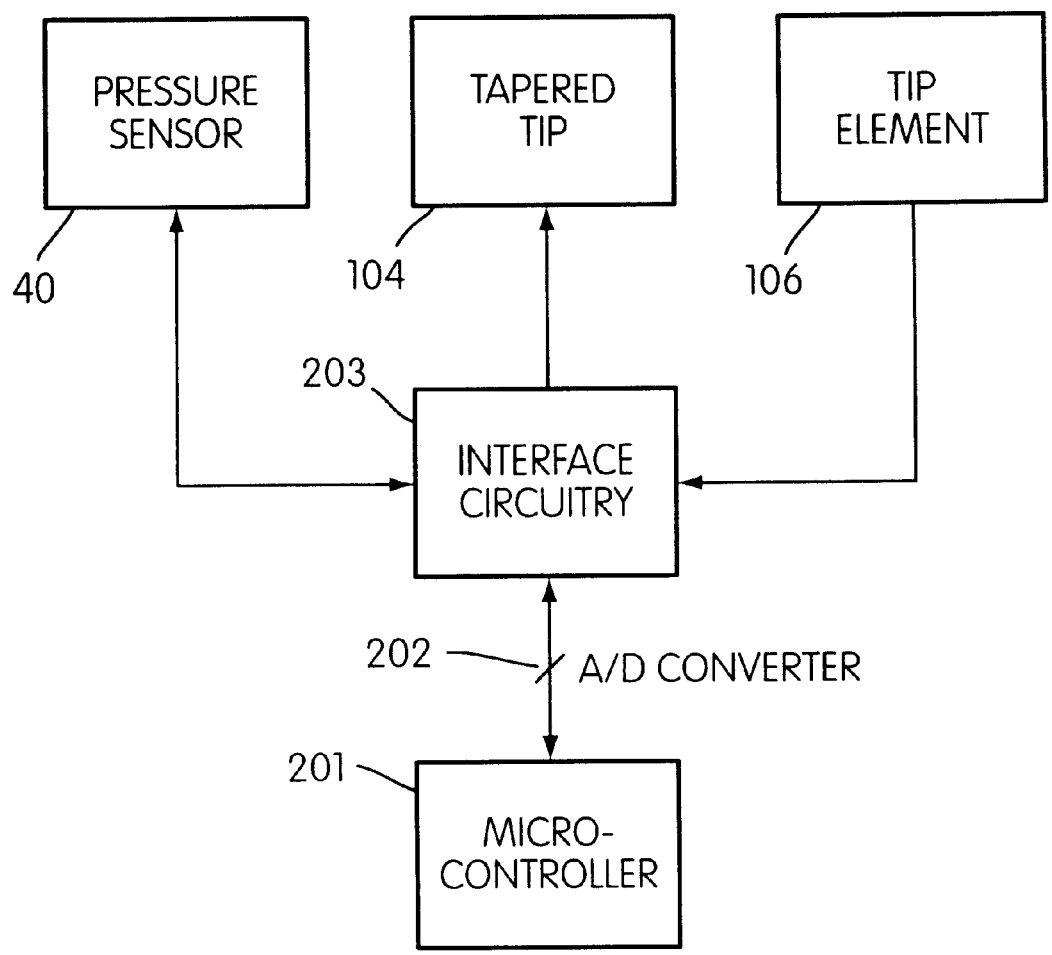
FIG. 10 is a block diagram illustrating the electrical sensing and detection circuitry in the dispense and surface verification system.

FIG. 10 is a high-level, block diagram illustrating the electrical sensing and detection circuitry of the dispense and surface verification system. Microcontroller 201, such as a model MC68HC16Z1 from the Motorola Corporation, is coupled, via the microcontroller's integral analog to digital converter, to interface circuitry 203, which interfaces with the sensor assembly 100 (FIG. 7) on fluid delivery probe 50. More particularly, the interface circuitry 203 drives an RF (radio frequency) excitation signal through transfer tube 102 and to tapered tip 104. The RF excitation signal transmitted by the tip 104 is received by the tip element 106, which acts as an antenna receiver. Pressure sensor 40 detects pressure changes created by fluid moving through the transfer tube 102 of the fluid delivery conduit assembly 52 and transmits a corresponding pressure signal to the interface circuitry 203.

Microcontroller 201 is shown connected to the interface circuitry 203 of a single fluid delivery probe 50.

Figure 11:
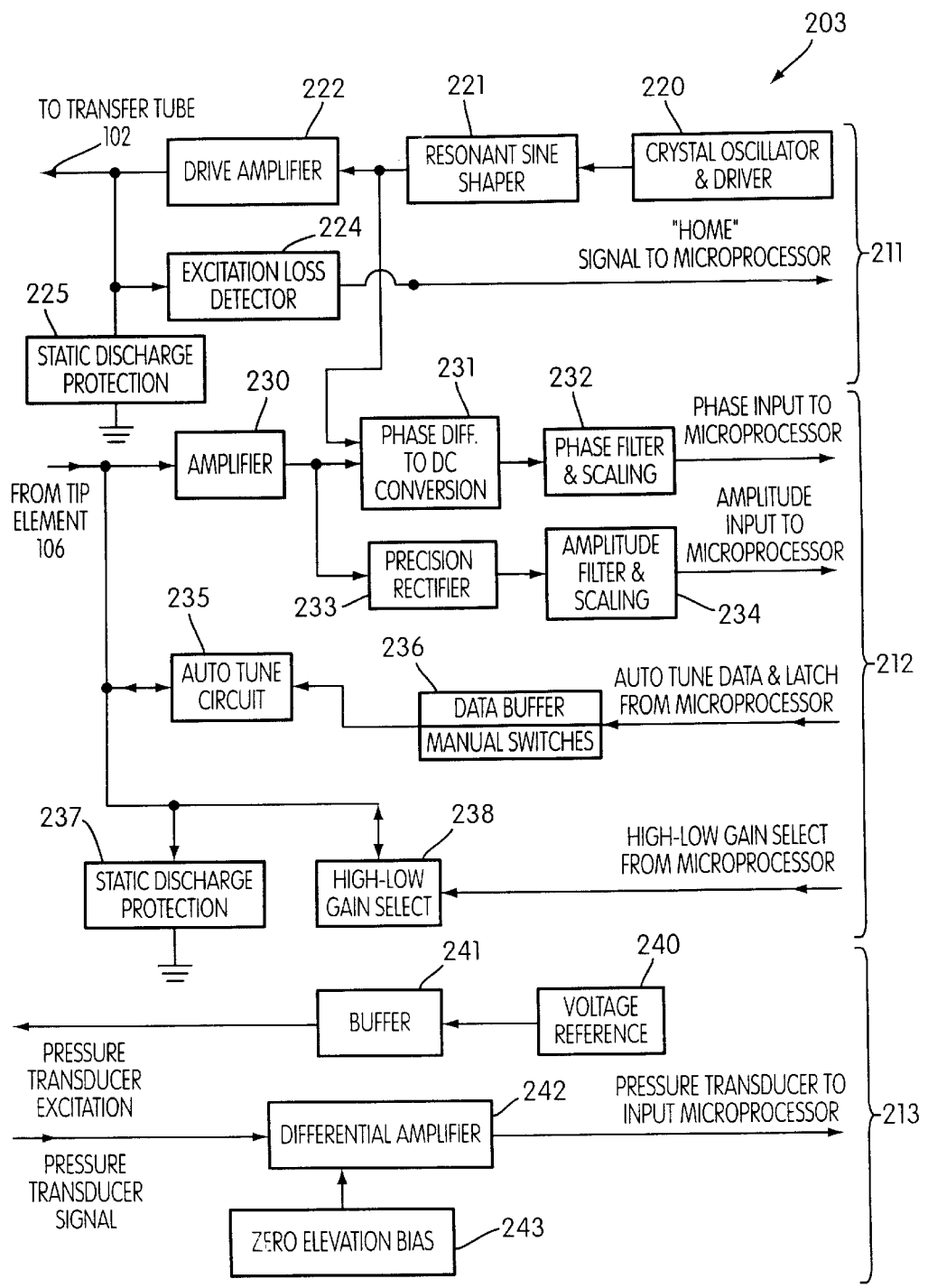
FIG. 11 is a detailed block diagram of a dispense and surface verification interface circuit.

FIG. 11 is a detailed block diagram of the interface circuitry 203. The circuit elements relating to the transfer tube 102, the tip element 106, and the pressure sensor 40 are generally grouped into element groups 211, 212, and 213, respectively.

The excitation signal transmitted through the transfer tube 102 is an RF signal, such as a signal in the vicinity of 100 KHz, generated by a crystal oscillator and frequency divider, generally indicated at 220, and processed by resonant sine shaper 221 and drive amplifier 222. The crystal oscillator/frequency divider 220 serves as the frequency source from which the transfer tube 102 (i.e., the transmitting electrode) excitation signal is generated. It comprises a crystal oscillator that operates at a higher than preferred frequency of 6 MHz, which is divided by 64 by a CMOS binary counter divider integrated circuit (74HC4060 manufactured by, e.g., Texas Instruments) to produce a frequency of near 100 KHz (actually 93.75 KHz). The signal output from crystal oscillator/frequency divider 220 is shaped into a sine wave by shaper 221 and then amplified by amplifier 222 before being supplied to the transfer tube 102. Amplifier 222 preferably includes circuitry that protects the amplifier from damage due to a short circuit. Suitable short-circuit protection circuitry would be well known to one of ordinary skill in the art and will not be discussed in detail herein. Crystal oscillators, sine wave shapers, and drive amplifiers are also well known in the art and will not be described in additional detail. The integrated divider circuit is a model 74HC4060 circuit, which also contains the active circuitry for the crystal oscillator. Such circuits are available from a number of vendors, such as, Harris Corporation of Melbourne, Fla. and Texas Instruments of Austin, Tex. One appropriate oscillator is manufactured by ECS Inc., International, of Olathe, Kans. as part number ECS-60-32-7. Sine wave shapers may be constructed from passive circuit components such as resistors, capacitors, and inductors. Drive amplifiers may be constructed using integrated circuit amplifiers available from a number of companies, one of which is National Semiconductor Corporation of Santa Clara, Calif.

When the fluid delivery probe 50 is in its "home" position (i.e., the position when fluid delivery probe 50 is at the upper limit of its mechanical motion in the direction of-the Z-axis), the transfer tube 102 is grounded through contact with the structural body of the substance transfer mechanism 20 because substance transfer mechanism 20 acts as a grounding potential. Excitation loss detector circuitry 224 is designed to detect the grounding of the excitation signal and then generate a corresponding home signal, which informs microcontroller 201 that the probe is in the home position to thereby stop the motor(s) driving upward Z-axis motion.

Diode clamping is implemented by static discharge protection circuitry 225 to protect elements 212 from excessive static discharge. Thus, excessive static electricity that accumulates on the transfer tube 102 will not damage the interface circuitry 203. In operation, if charge accumulates above a threshold level allowed by static discharge protection circuit 225, the diodes in circuit 225 shunt the excess charge to ground by way of positive and negative analog power supply rails (not shown). The threshold level is set low enough to protect elements 212 from damage.

Circuit elements 212 interact with tip element 106 via the signal transmitted from the tip element by the ribbon cable 66 and external cable 64. Elements 212 include an amplifier 230, a phase difference to DC conversion phase detector 231, a phase filter and scaling circuit 232, a precision rectifier 233, an amplitude filter and scaling circuit 234, an auto-tune circuit 235, a tuning information data buffer 236, static discharge protection circuitry 237, and a high-low gain select circuit 238. The interaction of tip element 106 and circuit elements 212 will be described in more detail below.

Tip element 106 acts as an antenna that receives RF signals transmitted from tapered tip 104 of the transfer tube 102. Signals received by the tip element 106 are amplified by amplifier circuit 230 before being supplied to phase detector 231 and precision rectifier 233. The phase detector 231 and precision rectifier 233 produce signals indicative of the phase change and the amplitude, respectively, of the signal received at tip element 106. By monitoring the temporal changes in these signals, microcontroller 201 detects changes caused by the presence or absence of fluids passing through the measurement section 122 between the tapered tip 104 and tip element 106 and/or caused by the tip element 106 contacting a fluid surface. Conductive fluids (ionic fluids), for example, when in contact with tapered tip 104 and tip element 106, effectively act as a conductor between the tip element 106 and tapered tip 104, thus increasing the measured amplitude of the signal received by the tip element 106. Less conductive fluids, on the other hand, tend to act more as a dielectric, thereby causing the tapered tip 104 and the tip element 106 to behave as electrodes of a capacitor, thus affecting the phase shift between the signal transmitted by the transfer tube 102 and the signal received by the tip element 106.

Phase detector 231 receives both the amplified tip element signal from the amplifier circuit 230 and the original transmission signal generated by sine shaper 221. Phase detector 231 compares the phase of the two signals and outputs a direct current (DC) signal having an amplitude corresponding to the phase difference between the two signals. The resultant signal is sent to microcontroller 201 by phase filter and scaling circuitry 232 after low-pass filtering and scaling to a level appropriate for transmission via the analog to digital converter 202. A more detailed description of phase detector 231 is given below with reference to FIG. 12.

Precision rectifier 233 also receives the output of amplifier circuit 230 and rectifies the signal so that only the positive portion of the signal is sent to amplitude filter and scaling circuit 234, which then low-pass filters the received signal to perform a DC averaging operation on the signal (i.e., the RF signal is converted to a DC signal of representative amplitude). This signal may then be scaled to a level appropriate for transmission to microcontroller 201 via analog to digital converter 202.

As described above, phase difference detector 231 and precision rectifier 233 operate in tandem to transmit both the phase shift and amplitude of signals received at tip element 106 to microcontroller 201. Microcontroller 201, by monitoring the temporal changes in signals received at tip element 106, discerns changes in the contact state and the ionic state of fluids in contact with the sensor assembly 100. Typically, the phase difference signal is monitored for fluid surface detection, and the amplitude signal is monitored for dispense verification as will be described in more detail below.

It is desirable to tune the receiver circuit formed by tip element 106, the ribbon cable 66, and coaxial cable 64, both to tune out undesirable capacitive reactance of ribbon cable 66 and the coaxial cable 64 and to initially tune the receiver circuit to be near resonance so that the phase shift between the signal transmitted by transfer tube 102 and the signal received by tip element 106 is small (e.g., about 10% or less and most preferable from 2–5%) or non-existent. Auto-tune circuit 235, which includes an inductor and a series of capacitors that operate as a variable capacitor, perform this tuning function. Typically, tuning is performed at system initialization (i.e., when the system is first turned on). Tuning may be performed only when significant components, e.g., probe 50, are replaced.

Tuning the circuit to near resonance is desirable because resonant circuits generate maximum amplitude signals and the maximum signal phase shift in response to excitation. Preferably, the circuit is tuned to a point slightly below resonance (e.g., 2–5% below resonance) in anticipation of the tip element 106 contacting a fluid surface and pushing the circuit towards resonance. Being tuned slightly below resonance, the receiver circuit operates in an area of its amplitude and phase resonant response curves where the change in amplitude and phase is monotonic.

Microcontroller 201, via the auto-tune circuit 235, tunes the circuit slightly below resonance by looking at the phase difference output by phase detector 231 during steady state conditions when no fluid is in contact with the sensor assembly 100. When the phase difference is zero, or nearly zero, the circuit is in resonance.

Physically, auto-tune circuit 235 may comprise an inductor (e.g., a 6.8 mH inductor) connected in parallel with a series of capacitors that are electrically inserted or removed from the circuit based on the data latched into data buffer 236. Microcontroller 201 monitors the phase difference output from phase filter and scaling circuit 232 and accordingly adjusts the variable capacitance of auto-tune circuit 235. The capacitance adjustment is performed using any of a number of known approximation algorithms (e.g., a binary approximation algorithm). Alternatively, instead of automatically adjusting the capacitance of auto-tune circuit 235, the circuit may be manually adjusted by selecting a series of manual switches, such as a DIP (dual in-line package) switch. A more detailed description of auto-tune circuit 235 is given below, with reference to FIG. 13.

Static discharge protection circuit 237, in a manner similar to static discharge protection circuit 225, protects circuit elements 213 from excessive static discharge.

Depending on the type of fluid (e.g., ionic or non-ionic) in contact with tip element 106 and/or tapered tip 104, the amplitude of the signals received by circuitry 212 may vary significantly in both surface sensing and volume verification applications. To effectively interpret such a large dynamic signal range, high-low gain select circuit 238, under control of microcontroller 201, dynamically adjusts (i.e., adjusts whenever necessary) the amplification level of amplifier 230. In operation, when the signal level received by microcontroller 201 from amplifier filter and scaling circuit 234 falls below a preset level, microcontroller 201 instructs high-low gain select circuit 238 to increase the gain of amplifier 230. Conversely, when the signal level received by microcontroller 201 from filter and scaling circuit 234 rises to its maximum level, microcontroller 201 instructs high-low gain select circuit 238 to decrease the gain of amplifier 230. High-low gain select circuit 238 is preferably implemented using a binary switch (transistor switched resistor) controlled by microcontroller 201 to switch between the high-gain state or low-gain state of circuit 238.

Pressure sensing circuitry elements 213 interact with microcontroller 201 and pressure sensor 40. More particularly, pressure at pressure sensor 40 changes as fluid is accelerated and decelerated through the tube 32 by pump 36. By monitoring changes in gauge pressure as detected by pressure sensor 40, the dispense and surface verification system can detect the onset of fluid being aspirated and dispensed. As will be described in more detail below, microcontroller 201 uses the information from pressure sensor 40 in combination with information derived from the signal received by tip element 106 to verify a proper fluid dispense by fluid delivery probe 50 (FIG. 3).

Pressure sensing circuitry elements 213 (FIG. 11) include a voltage reference circuit 240, a buffer 241, a differential amplifier 242, and zero elevation bias circuit 243. Voltage reference circuitry 240 generates a reference voltage that is buffered (temporarily stored) by buffer 241 before being transmitted to pressure sensor 40. The reference voltage generated by reference voltage circuitry 240 is used to calibrate the voltage output from the pressure sensor 40 to the desired output voltage range. Buffer 241 sources the reference voltage to sensor 40. Signals generated by pressure sensor 40 are amplified by differential amplifier 242 to a level appropriate for transmission to microcontroller 201 via analog to digital converter 202. The output of pressure sensor 40 is a function of both the changing fluid pressure in fluid delivery conduit assembly 52 caused by pump 36 and the quiescent fluid pressure of the fluid in the conduit assembly 52. Zero elevation bias circuit 243 compensates the signal from sensor 40 to set the value measured by differential amplifier 242 when the fluid is in its quiescent state to a predetermined value (e.g., 55 of a scale of 0 to 255).

Figure 12:
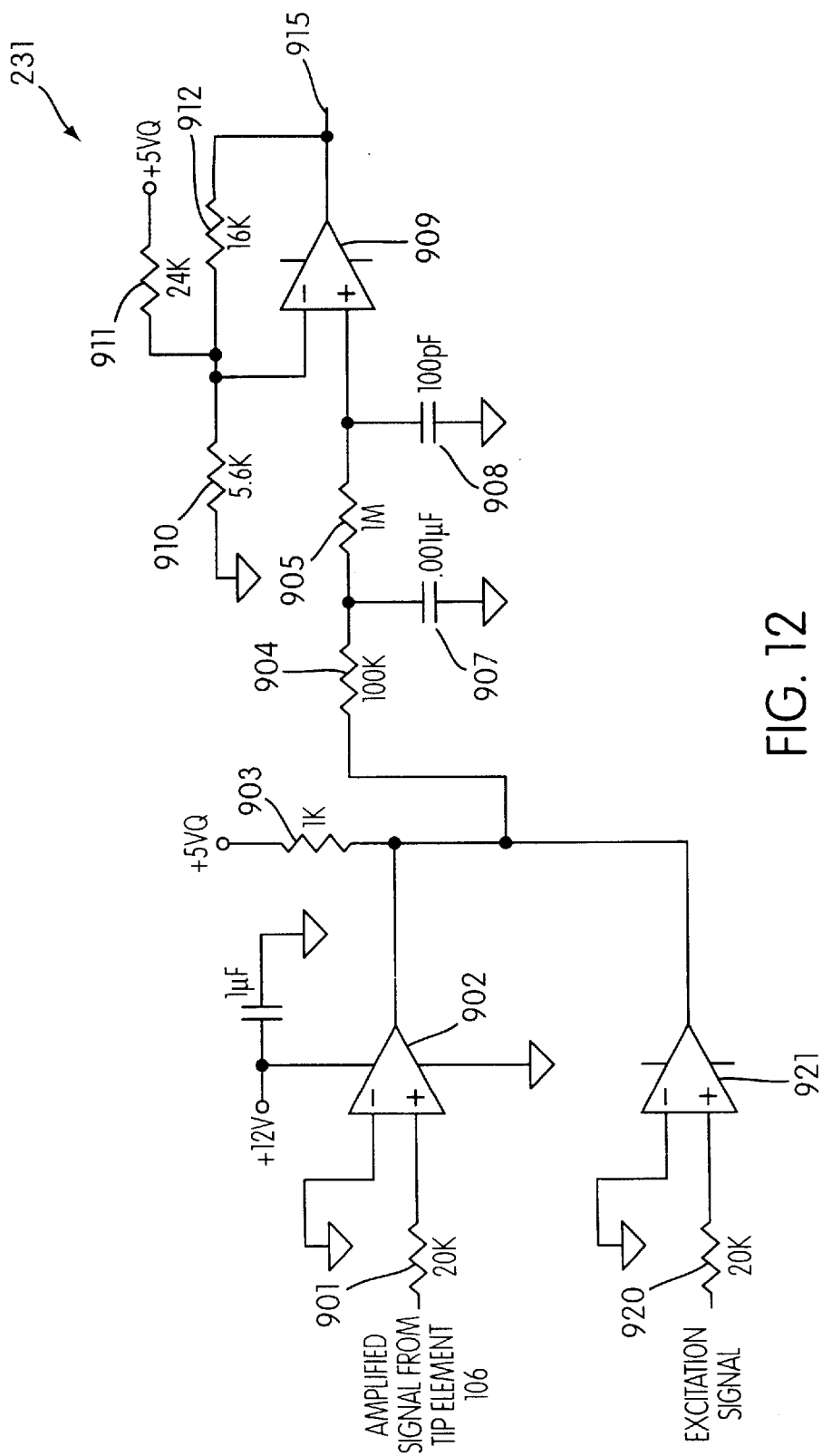
FIG. 12 is a circuit diagram of a phase detector circuit of the interface circuitry of the dispense and surface verification system.

FIG. 12 is a detailed circuit diagram illustrating an exemplary embodiment of the phase difference to DC conversion circuit 231. In general, conversion circuit 231 operates by converting its two input signals from sine shaper 221 and amplifier 230 to square waves, logically ANDing the two square waves, and averaging the logically ORed version of the signals to obtain an average DC value. The DC value is proportional to the phase difference between the two signals.

The signal received by the tip element 106 is passed through resistor 901 to comparator 902, which converts the input signal to a square wave. Similarly, the transmitted excitation signal is passed through resistor 920 to comparator 921, which converts the input signal to a square wave. The square waves are logically ANDed by resistor 903, and the resultant signal is then filtered by resistors 904 and 905 and by capacitors 907 and 908. Amplifier 909, in conjunction with resistors 910–912, implements an averaging circuit that averages the filtered signal to obtain the output signal 915.

In operation, the voltage of signal 915, when the input signals are in-phase, is half the pull-up voltage (shown as 5 volts), or 2.5 volts. As the phase between the two input signals shifts, the voltage of signal 915 varies. For example, for a phase shift of 90 degrees, the output voltage is one-quarter of 5 volts (1.25V). For a phase shift of 45 degrees, the output voltage is about 1.87 volts.

Appropriate resistance and capacitance values for the constituent resistors and capacitors of circuit 231 are shown in FIG. 12. Suitable comparators and amplifiers include, for example, models TLC372CD and TL074CD, respectively, available from Texas Instruments Inc., of Dallas, Tex. The resistors and capacitors are standard electronic components.

Figure 13:
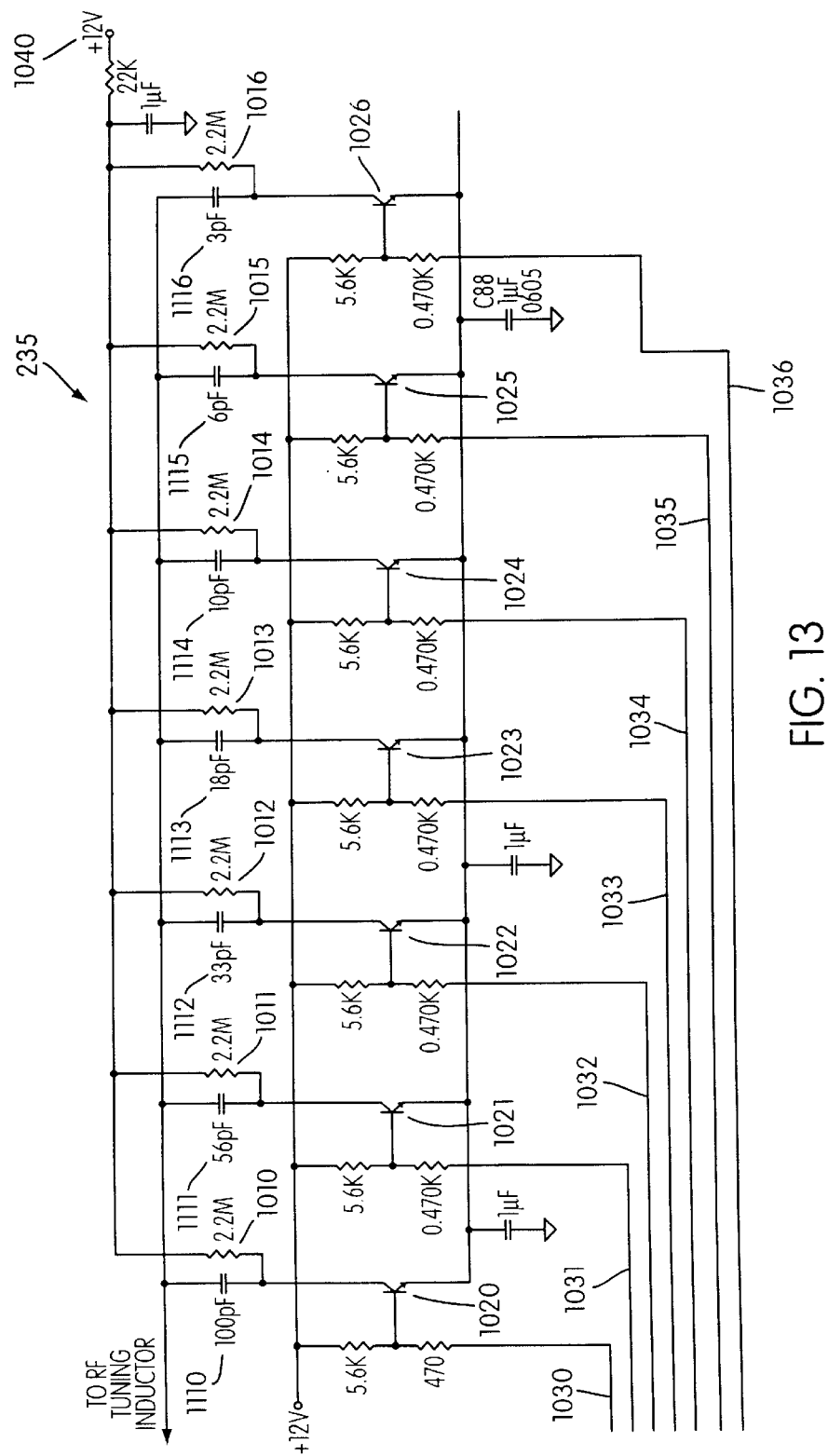
FIG. 13 is a circuit diagram of an auto-tune circuit of the interface circuitry.

FIG. 13 is a detailed circuit diagram illustrating an exemplary embodiment of the tuning portion of auto-tune circuitry 235.

As previously mentioned, microcontroller 201 dynamically tunes auto-tune circuit 235 by selecting a specific combination of capacitors 1110–1116 that generates a desired equivalent capacitance. Preferably, the capacitance of each of the capacitors 1110–1116 varies from one another based on a factor of a little less than two. For example, the illustrated capacitor values are: 100 pF (pico-Farad) (capacitor 1110), 56 pF (capacitor 1111), 33 pF (capacitor 1112), 18 pF (capacitor 1113), 10 pF (capacitor 1114), 6 pF (capacitor 1115), and 3 pF (capacitor 1116). Microcontroller 201 selects active combinations of these capacitors 1110–1116 by selectively activating or deactivating lines 1030–1036. Activation of any one of lines 1030–1036 causes associated transistors 1020–1026, respectively, to electrically couple or decouple one of capacitors 1110–1116 in the RF tuning portion of the circuit. Resistors 1010–1016 connect DC power source 1040 to a terminal of capacitors 1110–1116, respectively, and act to minimize collector to base capacitance effects of transistors 1020–1026.

Microcontroller 201, by selectively activating lines 1030–1036, can change the equivalent capacitance of capacitors 1110–1116 from about 3 pF to 200 pF. Alternate capacitive ranges could be implemented by substituting different values for capacitors 1110–1116.

Signal Processing and Analysis

The preferred manner in which signals generated by the sensor assembly 100 are used to sense a fluid surface and to confirm a proper fluid dispense will now be described.

In a typical aspirate/dispense sequence, the robotic substance transfer mechanism 20 moves the fluid delivery probe 50 to a container of fluid (e.g., an assay reagent) that is to be transferred from the container to a reaction receptacle (e.g., a test tube). After the fluid delivery probe 50 is positioned above the container, the substance transfer mechanism 20 lowers the fluid delivery probe 50 until the tip element 106 of the fluid delivery conduit assembly 52 contacts the fluid surface within the container, as sensed by the sensor assembly 100.

As described above, contact with a fluid surface can be sensed by monitoring the signal received by the tip element 106 and detecting a change in either the amplitude or the phase shift of the received signal that occurs when the tip element 106 contacts a fluid surface. Preferably, the fluid surface is sensed by monitoring the phase shift between the signal transmitted by the transfer tube 102 and the signal received by the tip element 106 and looking for a change in the phase shift that will occur when the tip element 106 contacts a fluid surface. Monitoring the phase shift is preferred because the change in phase shift resulting from fluid surface contact will typically be more drastic than a change in the amplitude of the received signal. Thus, it will be easier and more accurate to perform surface sensing by monitoring phase shift than by monitoring change in signal amplitude.

In particular, when there is no fluid in the measurement section 122 of the sensor assembly, 100, the tapered tip 104 of the transfer tube 102 and the tip element 106 are electrically coupled to each other only through a small capacitance arising from mutual physical proximity. The signal transmitted by transfer tube 102 will deviate slightly in phase from the signal received by the tip element 106, the deviation being due to slight off-resonance tuning of the resonant receiving arrangement described above. When the tip element 106 is not in contact with a fluid surface, the interface circuitry is switched to a high gain by the high-low gain select circuit 238, and the receiver circuit formed by the tip element 106, the ribbon cable 66, and the external coaxial cable 64 is tuned by the microcontroller 201 using the auto tune circuit 235 to near resonance (i.e., so that the phase shift between the transmitted and received signals deviates slightly from an in-phase condition as previously described). When the tip element 106 contacts a fluid surface, the phase shift signal detected by the phase detector 231 changes, deviating more greatly from an in-phase condition than was the case prior to fluid contact, thereby causing an almost immediate and easy to detect jump in the phase shift signal. This jump in the phase shift will indicate contact with a fluid surface.

The phase change is due to stray capacitance to ground of the sensed fluid and its container. When tip element 106 contacts the fluid surface, the effect is that of adding additional capacitance to ground from the tip due to the dielectric properties of the sensed fluid and its capacitive coupling to the metallic structure (i.e., ground). Thus, the resonant frequency of the tuned circuit decreases due to the added capacitance, changing both the phase and amplitude of the signal at the tip element.

When sensing very conductive fluids in this manner, the effect is that of increasing stray capacitance yet more, as the interface surface area between the fluid and its (non-conductive) container serves as one plate of a better defined, larger capacitor, with the other plate being the surrounding metallic (ground) structure. This is true as a container of very conductive fluid behaves electrically almost in the manner of a solid metallic block, i.e., it is conductive to the point where conductivity within the liquid completely overrides dielectric (internal capacitance) effects.

A change in amplitude arises due to a greater departure from resonance than is implemented and fixed by the autotuning algorithm. Operation in this manner is akin to slope detection, known to those skilled in the art, where detection of frequency deviation utilizes skirt slopes of resonant response curves for conversion of frequency deviation to amplitude deviation.

When contact with the fluid surface is detected, descent of the fluid delivery probe 50 is arrested, so that the position of the tip of the fluid delivery conduit assembly 52 is maintained at or just below the fluid surface. Next, the pump 36 is activated to draw (i.e., aspirate) an aliquot of fluid from the container and into the fluid delivery conduit assembly 52. It may be desirable to transfer multiple aliquots of fluid from the container to multiple reaction receptacles. Thus, more than one aliquot may be drawn into the fluid delivery conduit assembly 52 so that the multiple aliquots can be dispensed into multiple reaction receptacles without requiring repeated returns to the container for each aliquot to be dispensed. Depending on the volume of fluid drawn by the pump 36 and the respective volumes of the fluid delivery conduit assembly 52, the rigid tube extension 34, and the flexible tube 32, fluid may be drawn by the pump 36 up into the rigid tube extension 34 and-the flexible tube 32.

In the preferred manner of practicing the invention, the pump 36 and part of the fluid conduit defined by the flexible tube 32 and the rigid tube extension 34 are filled with deionized water to function as a drawing, or pumping, fluid when the pump 36 is activated to draw fluid from a container into the fluid delivery conduit assembly 52. Deionized water is used because, compared to air, it is incompressible and therefore better suited than air to function as a drawing fluid for aspirating and dispensing precise amounts of fluid. To prevent the aspirated fluid from becoming contaminated by the water in the fluid conduit, an air gap is maintained within the fluid conduit between the deionized water and the aspirated fluid.

When fluid is drawn by the pump 36 into the fluid delivery probe 50, the pressure sensor 40 will detect a change in gauge pressure when a fluid (e.g., pure liquid, solution, mixture, slurry, suspension, etc.) is aspirated into the fluid delivery probe 50. This measurable change in pressure can be used to confirm that fluid has indeed been aspirated, and certainly, if only air were aspirated, the sensor 40 would be able to provide an indication of this fact because there would be essentially no change in gauge pressure. On the other hand, if a partial or incomplete aspiration occurred, for example, if there were foam at the surface of the fluid so that some amount of air were aspirated in addition to the fluid, the sensor 40 may still detect a measurable change in pressure. This can happen because, when performing a surface sensing function, the dispense and surface verification system does not necessarily have the ability to distinguish between foam and fluid. Thus, if the sensor assembly 100 contacts foam at the fluid surface, the resulting phase shift of the signal received by the tip element 106 may be sufficient to give a positive fluid surface indication, even if the assembly 100 has not actually contacted the fluid surface.

If at least some fluid were aspirated, along with the foam (i.e., a combination of air and fluid), the magnitude of the pressure change may be large enough to erroneously indicate a proper aspiration. Proper aspiration could be verified by monitoring the period of time that the sensor 40 indicates a pressure change that is above a predefined threshold indicative of proper fluid aspiration. If the pressure change lasts for an expected period of time within a predefined limit, proper aspiration of a sufficient quantity of fluid can be confirmed. If, due to the partial aspiration of air, the pressure change does not last for an expected period of time, an improper aspiration is indicated, and an error code would be returned.

In the preferred manner of practicing the present invention, the line pressure measured by the sensor 40 is not monitored during fluid aspiration. Rather, proper fluid aspiration is confirmed indirectly by confirming proper dispense of the prescribed amount of each aliquot of fluid, as will now be described.

After one or more aliquots of fluid have been aspirated, the robotic substance transfer mechanism 20 moves the fluid delivery probe 50 to a reaction receptacle and positions the fluid delivery conduit assembly 52 for dispensing fluid into the reaction receptacle. The accuracy and integrity of results obtained from tests performed in the reaction receptacle(s) are dependent on, among other factors, dispensing the proper amount of each assay reagent into the receptacle(s). In other applications involving the fluid dispense and fluid surface verification device and method of the present invention, the accuracy of test results may not be at stake, but verification of proper fluid dispense may, nonetheless, be important. Regardless of the application, the present invention provides an apparatus and method for accurately verifying a proper dispense of fluid.

During fluid dispense, the pump 36 is activated for a discrete period in order to force a discrete amount of fluid through the fluid delivery conduit assembly 52 and into an awaiting receptacle. Movement of fluid through the conduit assembly 52 under the force of the pump 36 will cause a measurable increase in the fluid pressure, as sensed by the pressure sensor 40. Similarly, movement of fluid through the measurement section 122 of the sensor assembly 100 will cause a measurable change in the amplitude and/or the phase of the signal received by the tip element 106.

Furthermore, the fluid dispense verification capability of the system is preferably used to verify the passage of a cleansing fluid, such as deionized water, through the probe assembly 52 in response to the action of a pump constructed and arranged to move such cleansing fluid through the assembly 52.

Figure 14:
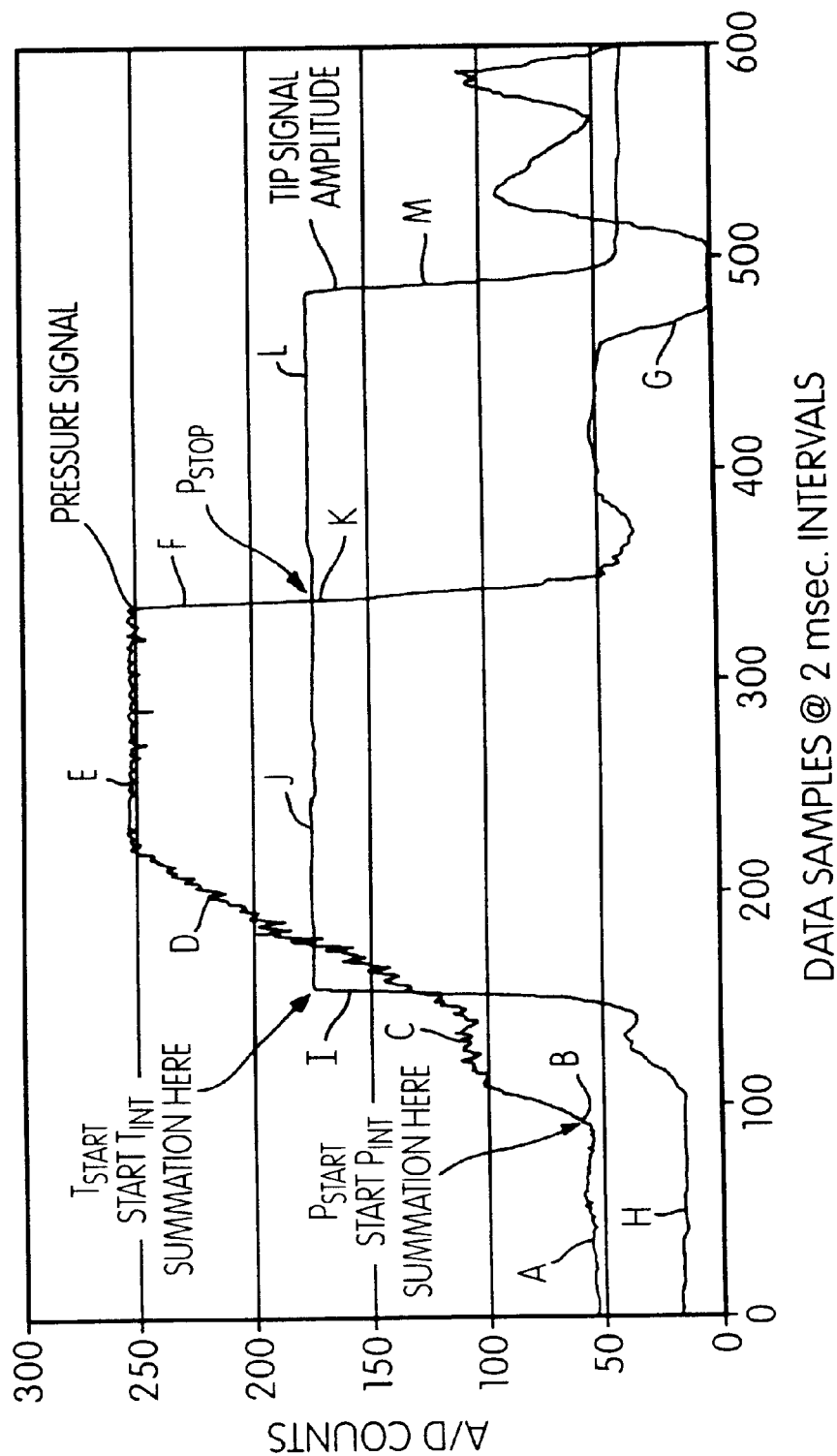
FIG. 14 shows plots of a typical pressure time signal and a typical sensor assembly time signal generated by the dispense and surface verification system.

FIG. 14 shows exemplary pressure sensor and tip element signals superimposed on a dimensionless amplitude (analog to digital, or "A/D", counts) versus time (discrete data samples @ 2 msec intervals) plot for a normal dispense sequence of a particular fluid. A travel gap is employed in the dispense sequence represented in the plots of FIG. 14. A travel gap is a pocket of air that is drawn into the conduit assembly 52 through the tip element 106 and resides between the distal end of the tip element 106 and the bottom surface of a fluid previously drawn into and contained within the assembly 52. The purpose of the travel gap is to prevent hanging drops of fluid from dislodging when the probe 50 is being moved from a fluid container to a reaction receptacle. While the size of the air gap is not critical it should be of sufficient volume to prevent the release of any fluid from the tip element 106 when the probe 50 is in transit.

Before the pump 36 is activated to dispense fluid, both the pressure signal and the tip signal exhibit a steady quiescent state, generally indicated by the portions A and H, respectively, of the pressure signal and the tip signal shown in FIG. 14. When the pump 36 is first activated to dispense, the pressure signal exhibits an increase at an inflection point indicated at B. The pressure signal exhibits a positive slope as the pump accelerates toward its final velocity. It has been noted during experiments that the pressure signal will exhibit an interruption, generally indicated at C, in the positive slope during pump acceleration. It is believed that this is due to the fact that during initial pump acceleration, the travel gap is being forced out of the fluid delivery conduit assembly 52, and, due to the compressibility of the air in the travel gap, the pressure signal slope decreases briefly until the travel gap is forced out of the conduit assembly 52. In fact, in dispensing experiments in which there is no travel gap in the fluid delivery conduit assembly, it has been noted that the pressure signal does not exhibit this interruption during pump acceleration.

After the interruption C, the pressure signal exhibits a substantially constant positive slope, indicated at D, that is directly related to the acceleration of the pump. When the pump reaches and maintains its maximum velocity, the pressure signal levels off as indicated at E. The pump is operated at its maximum velocity for a prescribed period of time to dispense an aliquot of fluid and is then stopped. When the pump stops, the pressure in the system conduit, and thus the pressure signal, drops almost instantaneously, as shown at F, back toward its quiescent level. Shortly after dispensing is terminated by stopping the pump, if fluid remains in the conduit assembly 52, the pump is activated in a reverse direction to generate a drop in system pressure, as shown at G, to thereby draw a travel air gap into the conduit assembly 52 before moving the fluid delivery probe 50 to the next receptacle that is to receive an aliquot of fluid.

The tip signal, which is the amplitude of the signal received by the tip element 106 of the sensor assembly 100, is an indication of when there is a conductive path through the measurement section 122 connecting the distal end 124 of the transfer tube 102 and the proximal end 126 of the tip element 106. For non-conductive fluids a similar signal of phase shift vs time would be analyzed.

In the embodiment of the sensor assembly 100' shown in FIG. 9, the measurement section 122 is defined between the distal end 124 of the tapered tip 104 of the transfer tube 102 and an exposed section 108' of the tip element 106' at the end of the isolating sleeve 112. Otherwise, the sensor assembly 100' operates similarly to the sensor assembly 100 in the sense that the tapered tip 104 functions as a signal transmitting electrode and the tip element 106' functions as a signal receiving electrode that is electrically isolated from the tapered tip 104. One benefit of the sensor assembly 100' shown in FIG. 9 over the sensor assembly 100 shown in FIG. 7 is that the proximal end 126' of the tip element 106' of the assembly 100' is outside the fluid flow path. On the other hand, the proximal end 126 of the tip element 106 of the assembly 100 is inside the fluid flow path and thus forms a surface where fluid buildup can potentially occur.

As shown in FIG. 14, the tip signal remains substantially at its quiescent level, indicated at H, for a brief period after the pressure signal has started rising. Due to the travel air gap, there is a brief period after the pump is activated during which the measurement section 122 is not full of fluid, so there is no conductive connection between the transfer tube 102 and the tip element 106. After the travel gap has been forced through the measurement section 122, the tip signal amplitude jumps almost instantaneously, as shown at I, to its maximum level indicating conduction (i.e., a short) between the transfer tube 102 and the tip element 106. The tip signal amplitude will exhibit this steady state level, as shown at J, as long as there is a conductive fluid in the measurement section 122.

In fact, in a proper dispense, where there are multiple aliquots to be dispensed, the tip signal amplitude will maintain this level for a period after the pump stops, as shown at L after the tip signal has intersected the pressure signal, until a travel air gap is drawn into the conduit assembly 52 to break the conduction between the transfer tube 102 and the tip element 106 to thereby cause the tip signal amplitude to drop almost instantaneously, as shown at M.

It has been empirically determined by monitoring abnormal dispenses created by simulating system malfunctions, such as fluid foaming, loose fluid conduit fittings, and low system fluid level, that abnormal dispenses can be detected by monitoring and evaluating four features of the pressure and tip signals: 1) the pressure pulse width ($P_{PW}$); 2) the pressure signal integral ($P_{int}$); 3) the tip signal amplitude variability; and 4) the tip signal amplitude integral.

The pressure pulse width ($P_{PW}$) is the width (along the time axis) of the pressure signal from the beginning of the pressure pulse rise ($P_{start}$), point B, to the sharp fall when the pump stops ($P_{stop}$), point F. Ideally, to find $P_{start}$, a window is set around the expected pressure signal transition and the data points in the window are evaluated and compared to a threshold value to determine if the transition occurs. Preferably, the dispense and surface verification system is in communication with the pump so the system will "know" when to expect a transition in the pressure signal based on activation of the pump. A threshold value may be defined by averaging a suitable number (e.g., 16) of data points taken during the quiescent portion of the pressure data before the pump has been activated and adding a prescribed number (e.g. 20) to the quiescent average. For example, if the average value of the pressure data during the quiescent portion of the signal were 40 A/D counts, the threshold value may be set at 60 A/D counts. When the pressure data exceeds the predefined threshold, a pressure transition is indicated and $P_{start}$ is located.

Similarly, $P_{stop}$ may be defined at the point where the pressure value falls below the threshold level or some other predefined percentage of the maximum pressure, for example 50% of the maximum pressure value.

Another method for finding $P_{start}$ and/or $P_{stop}$ would be to perform a slope detection function on sliding groups of data points near expected pressure transitions until a sharp change in the slope is detected. For example, $P_{stop}$ can be found by centering a window of suitable width at a point spaced from $P_{start}$ by the anticipated pulse width and searching for a radical downward transition (i.e., a slope change) in the pressure signal. If the transition is found, record $P_{stop}$ at the beginning of the transition. If no transition is found, an error code is returned.

Assuming that $P_{stop}$ and $P_{start}$ are found, the pulse width, $P_{stop}-P_{start}$, is compared to experimentally-determined low and high limits of the pulse width designated $P_{PWLO}$ and $P_{PWHI}$, respectively. The limits $P_{PWHI}$ and $P_{PWLO}$ are unique to each reagent that may be transferred with the fluid delivery probe 50 and can be downloaded into or previously stored in the dispense and surface verification diagnostic software.

If $P_{PW}$ is within the expected limits, the pressure signal is integrated ($P_{int}$) from $P_{start}$ to $P_{stop}$, That is, the area under the pressure signal curve between $P_{start}$ and $P_{stop}$ is computed. $P_{int}$ is defined as the sum of all of the discrete data pressure points during pump operation. More particularly, $P_{int}$ is determined by subtracting the base line area under the curve from the integral calculated from $P_{start}$ to $P_{stop}$. The base line area under the curve, i.e., the baseline integral, is obtained by multiplying the average baseline pressure signal value (before pumping started) by the derived pulse width, $P_{PW}$. Experimentally-determined limits $P_{intLO}$ and $P_{intHI}$, which are also unique for each reagent, are downloaded into or stored in the dispense and surface verification diagnostic software, and the calculated $P_{int}$ is evaluated to determine whether it is within these limits. If $P_{int}$ is within the expected limits, processing may continue; if not, an error code is returned.

Normally the integral of a pressure versus time signal (i.e., the area under the pressure-time signal) would be equal to the volume of fluid dispensed during pump movement. In the preferred application of the dispense and surface verification system of the present invention, however, the pressure and tip signals are recorded merely as dimensionless A/D counts to provide indications of relative changes in the respective signals, without indicating the actual magnitudes of the respective signals. A dispense and surface verification system may be modified, however, by providing system calibration so that pressure signal voltage is converted to actual pressure magnitude. Thus, the pressure signal integral, calculated as described above, would provide the volume of fluid dispensed during pump movement.

The tip signal integral is designated $T_{int}$ and is defined as the sum of the tip amplitude signal data points starting at the rising transition of the tip signal, section I, designated $T_{start}$, and ending at $P_{stop}$. In other words, the integral is calculated for the time during which fluid is actually flowing through the measurement section 122. $T_{start}$ can be determined by monitoring the tip signal amplitude and designating $T_{start}$ as that point where the tip signal data exceeds a predefined threshold, as described above with respect to $P_{start}$. Alternatively, $T_{start}$ can be located by performing a slope detection function on the tip signal data and locating a sharp transition (i.e., jump in slope). As with the pressure integral $P_{int}$, the tip signal integral $T_{int}$ can be determined by simple integration.

$T_{int}$ is calculated from $T_{start}$ to $P_{stop}$ and is compared against experimentally-determined limits $T_{intLO}$ and $T_{intHI}$, which are unique to each reagent. If $T_{int}$ is not within the expected limits, an error code is returned.

An irregularity in the tip signal, which is indicative of a discontinuity in fluid flow between the tapered tip 104 and the tip element 106 (due to, e.g., pump malfunction, probe blockage, air bubbles in the dispensed fluid, insufficient fluid available for dispensing), will result in a value of $T_{int}$ that is not within expected limits. On the other hand, a value of $T_{int}$ that is within expected limits is indicative of a regular tip signal and thus a proper fluid dispense.

If no travel air gap is employed, fluid fully fills the measurement section 122 prior to pumping, so there will be no transition in the tip signal amplitude. Thus, $T_{start}$ cannot be determined by comparing tip signal data to a threshold value or by preforming a slope detection. The starting point, $T_{start}$ for determining $T_{int}$, can be defined some time after $P_{start}$ by moving out a predetermined number of data samples from $P_{start}$. The number of samples can be determined experimentally from typical data (it will be reagent-specific) and represents the time before fluid would have reached the measurement section 122 if there had been a travel gap. Ideally, the starting point, $T_{start}$, selected should correspond to the beginning of a fluid dispense.

Figure 15:
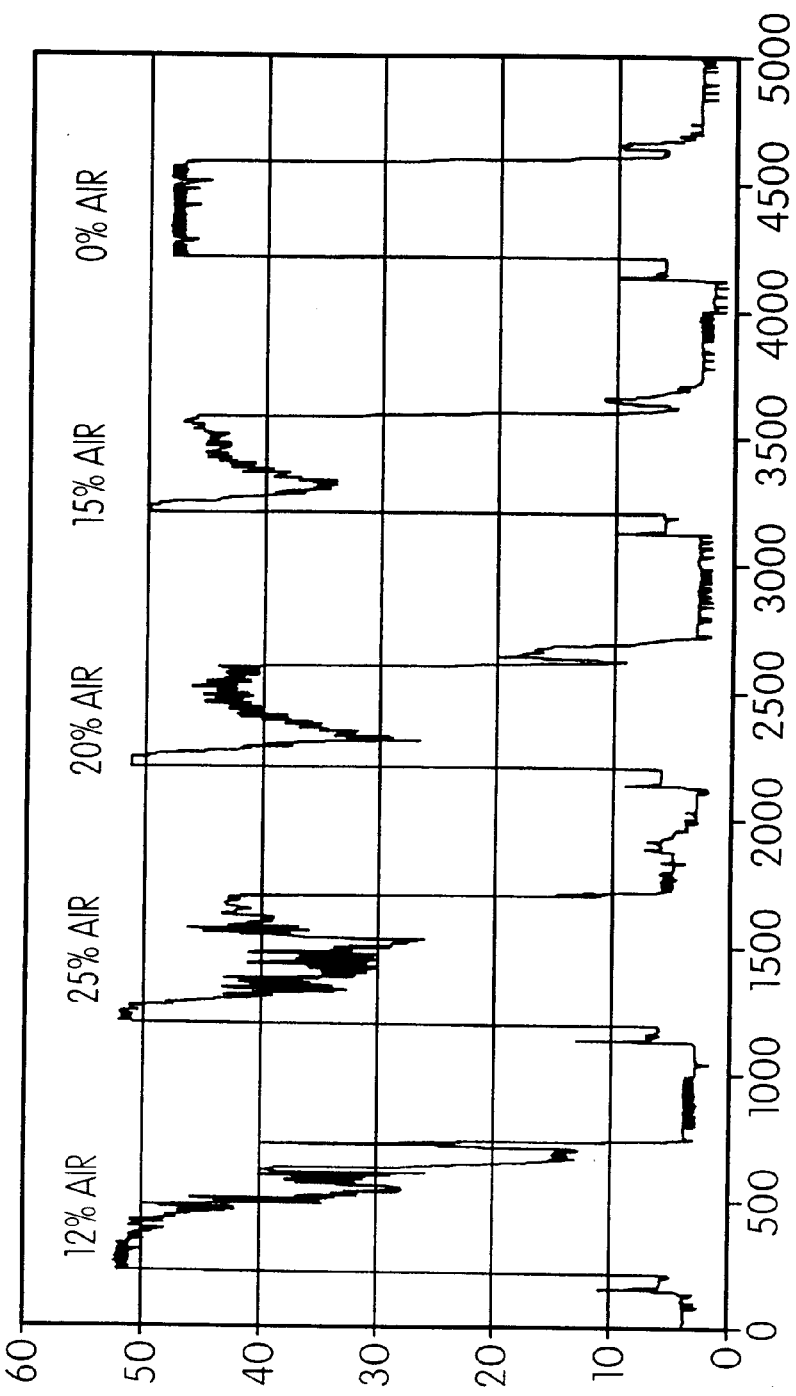
FIG. 15 shows plots of pressure-time signals as affected by varying amounts of air entrained in fluid moving through the fluid delivery system.

The tip signal amplitude variability is indicated by $T_{hcv}$ (derived from coefficient of variance of the horizontal tip signal). During a normal dispense, once fluid fills the measurement section 122 of the sensor assembly 100 during pump acceleration, the tip signal should be substantially constant through the end of pump movement or $P_{stop}$, as demonstrated by section J of the tip signal of FIG. 14. If the tip signal is not substantially constant, this is an indication that fluid flow through the measurement section 122 is not constant, a condition that can occur if air bubbles are aspirated into the system. For example, see FIG. 15, which shows exemplary pressure signals for fluid dispenses in which various amounts of air are trapped in the fluid. Air bubbles being aspirated into the system often result from a faulty surface sense prior to fluid aspiration, where aspiration is commenced when the tip of the probe assembly 52 is slightly above the fluid surface.

$T_{hcv}$ is determined by evaluating the tip signal data points starting just beyond the rising transition, where the tip signal integral summation is started, and continuing until $P_{stop}$. The standard deviation of the points divided by the mean of all the data points results in $T_{hcv}$, and is expressed as a percent. For each reagent, a maximum tip signal variability $T_{hcvMax}$ is determined experimentally, and the calculated $T_{hcv}$ is compared to this maximum.

If $T_{hcv}$ is above an expected $T_{hcvMax}$, an error code is returned. The variability that can be tolerated will depend on the particular application.

While the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. §112(¶6), are not intended to be interpreted under 35 U.S.C. §112(X̶6) as being limited to the structure, material, or acts described in the present specification and their equivalents.

What is claimed is:

1. A method of detecting fluid flow through a conduit due to the operation of a fluid pump to determine if a predetermined amount of a fluid was moved through the conduit by operation of the pump comprising measuring pressure within the conduit and determining a duration of an increase in pressure within the conduit associated with fluid movement through the conduit due to the operation of the pump and comparing the determined duration of increased pressure to a duration that would be expected if the predetermined amount of fluid were moved through the conduit, wherein the duration of the increase in pressure is determined by:

determining a pressure increase time corresponding to an initial increase in pressure associated with initiation of forced fluid movement through the conduit;

determining a pressure drop time corresponding to a drop in pressure below an increased pressure value associated with forced fluid movement through the conduit; and subtracting the pressure increase time from the pressure drop time.

2. The method of claim 1, further comprising comparing the determined duration of increased pressure to a range of durations that would be expected if the predetermined amount of fluid were moved through the conduit.

3. The method of claim 1, further comprising calculating a time integral of a pressure signal over a period of increased pressure within the conduit associated with forced fluid movement through the conduit due to operation of the pump and comparing the calculated integral to a value that would be expected if the predetermined amount of fluid were moved through the conduit.

4. The method of claim 3, further comprising comparing the calculated integral to a range of values that would be expected if the predetermined amount of fluid were moved through the conduit.

5. The method of claim 1, wherein at least a portion of the conduit comprises a fluid delivery probe and the duration of increased pressure is measured while fluid is being dispensed from the probe due to the operation of the pump.

6. The method of claim 1, wherein said measuring pressure comprises measuring fluid pressure within the conduit.

7. The method of claim 1, further comprising determining the magnitude of the increase in pressure within the conduit associated with fluid movement through the conduit due to the operation of the pump and comparing the determined magnitude of increased pressure to a magnitude that would be expected if the predetermined amount of fluid were moved through the conduit.

8. The method of claim 7, wherein determining the magnitude of the increase in pressure comprises calculating a time integral of a pressure signal over a period of increased pressure within the conduit associated with forced fluid movement through the conduit due to operation of the pump, and comparing the determined magnitude comprises comparing the calculated integral to a value that would be expected if the predetermined amount of fluid were moved through the conduit.

* * * * *